US012508058B2

(12) United States Patent
Cheng et al.

(10) Patent No.: US 12,508,058 B2
(45) Date of Patent: Dec. 30, 2025

(54) ADJUSTABLE TETHER IMPLANT

(71) Applicant: NuVasive Specialized Orthopedics, Inc., San Diego, CA (US)

(72) Inventors: Shanbao Cheng, Rancho Santa Margarita, CA (US); Joon An, Buena Park, CA (US); Michael Moeller, Carlsbad, CA (US); Shawn Placie, Aliso Viejo, CA (US); Jorge Lopez Camacho, Oxnard, CA (US); Woong Kim, Irvine, CA (US); Emmon Chen, Aliso Viejo, CA (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 211 days.

(21) Appl. No.: 18/464,451

(22) Filed: Sep. 11, 2023

(65) Prior Publication Data

US 2024/0115300 A1 Apr. 11, 2024

Related U.S. Application Data

(60) Provisional application No. 63/378,787, filed on Oct. 7, 2022.

(51) Int. Cl.

| | |
|---|---|
| *A61B 17/84* | (2006.01) |
| *A61B 17/56* | (2006.01) |

(52) U.S. Cl.

CPC ............ *A61B 17/844* (2013.01); *A61B 17/56* (2013.01); *A61B 2017/564* (2013.01)

(58) Field of Classification Search

CPC .............. A61B 17/844; A61B 17/7001; A61B 17/7002; A61B 17/7005; A61B 17/7019; A61B 17/7029; A61B 17/7031

See application file for complete search history.

(56) References Cited

U.S. PATENT DOCUMENTS 2,702,031 A 2/1955 Wenger
3,111,945 A 11/1963 Von Solbrig
(Continued)

FOREIGN PATENT DOCUMENTS

CN 1697630 A 11/2005
CN 101040807 A 9/2007
(Continued)

OTHER PUBLICATIONS

Abe et al., "Experimental external fixation combined with percutaneous discectomy in the management of scoliosis.", Spine, 1999, pp. 646-653, 24, No. 7.

(Continued)

*Primary Examiner* — Ellen C Hammond

(57) ABSTRACT

An adjustable implant system configured to non-invasively guide bone growth in a patient. The adjustable implant system includes a tether having a first end coupled to a fixed bone anchor and a second end coupled to an adjustable bone anchor. The adjustable bone anchor includes a driver disposed within a housing and the driver is configured to actuate in response to an externally applied magnetic field. The adjustable implant system includes an external adjustment device configured to non-invasively actuate the driver disposed within the adjustable bone anchor. Non-invasive actuation of the driver can cause the adjustable bone anchor to increase or decrease the amount of tension on the tether.

20 Claims, 18 Drawing Sheets

(56) References Cited

U.S. PATENT DOCUMENTS

| | | | |
|---|---|---|---|
| 3,372,476 | A | 3/1968 | Peiffer |
| 3,377,576 | A | 4/1968 | Langberg |
| 3,512,901 | A | 5/1970 | Law |
| 3,597,781 | A | 8/1971 | Eibes |
| 3,900,025 | A | 8/1975 | Barnes, Jr. |
| 3,915,151 | A | 10/1975 | Kraus |
| RE28,907 | E | 7/1976 | Eibes et al. |
| 3,976,060 | A | 8/1976 | Hildebrandt et al. |
| 4,010,758 | A | 3/1977 | Rockland et al. |
| 4,056,743 | A | 11/1977 | Clifford et al. |
| 4,068,821 | A | 1/1978 | Morrison |
| 4,078,559 | A | 3/1978 | Nissinen |
| 4,204,541 | A | 5/1980 | Kapitanov |
| 4,357,946 | A | 11/1982 | Dutcher et al. |
| 4,386,603 | A | 6/1983 | Mayfield |
| 4,448,191 | A | 5/1984 | Rodnyansky et al. |
| 4,486,176 | A | 12/1984 | Tardieu et al. |
| 4,501,266 | A | 2/1985 | McDaniel |
| 4,522,501 | A | 6/1985 | Shannon |
| 4,537,520 | A | 8/1985 | Ochiai et al. |
| 4,550,279 | A | 10/1985 | Klein |
| 4,561,798 | A | 12/1985 | Elcrin et al. |
| 4,573,454 | A | 3/1986 | Hoffman |
| 4,592,355 | A | 6/1986 | Antebi |
| 4,595,007 | A | 6/1986 | Mericle |
| 4,642,257 | A | 2/1987 | Chase |
| 4,658,809 | A | 4/1987 | Ulrich et al. |
| 4,700,091 | A | 10/1987 | Wuthrich |
| 4,747,832 | A | 5/1988 | Buffet |
| 4,854,304 | A | 8/1989 | Zielke |
| 4,904,861 | A | 2/1990 | Epstein et al. |
| 4,931,055 | A | 6/1990 | Bumpus et al. |
| 4,940,467 | A | 7/1990 | Tronzo |
| 4,957,495 | A | 9/1990 | Kluger |
| 4,973,331 | A | 11/1990 | Pursley et al. |
| 5,010,879 | A | 4/1991 | Moriya et al. |
| 5,030,235 | A | 7/1991 | Campbell, Jr. |
| 5,041,112 | A | 8/1991 | Mingozzi et al. |
| 5,064,004 | A | 11/1991 | Lundell |
| 5,074,882 | A | 12/1991 | Grammont et al. |
| 5,092,889 | A | 3/1992 | Campbell, Jr. |
| 5,133,716 | A | 7/1992 | Plaza |
| 5,142,407 | A | 8/1992 | Varaprasad et al. |
| 5,156,605 | A | 10/1992 | Pursley et al. |
| 5,263,955 | A | 11/1993 | Baumgart et al. |
| 5,290,289 | A | 3/1994 | Sanders et al. |
| 5,306,275 | A | 4/1994 | Bryan |
| 5,330,503 | A | 7/1994 | Yoon |
| 5,334,202 | A | 8/1994 | Carter |
| 5,336,223 | A | 8/1994 | Rogers |
| 5,356,411 | A | 10/1994 | Spievack |
| 5,356,424 | A | 10/1994 | Buzerak et al. |
| 5,364,396 | A | 11/1994 | Robinson et al. |
| 5,403,322 | A | 4/1995 | Herzenberg et al. |
| 5,429,638 | A | 7/1995 | Muschler et al. |
| 5,437,266 | A | 8/1995 | McPherson et al. |
| 5,466,261 | A | 11/1995 | Richelsoph |
| 5,468,030 | A | 11/1995 | Walling |
| 5,480,437 | A | 1/1996 | Draenert |
| 5,509,888 | A | 4/1996 | Miller |
| 5,516,335 | A | 5/1996 | Kummer et al. |
| 5,527,309 | A | 6/1996 | Shelton |
| 5,536,269 | A | 7/1996 | Spievack |
| 5,549,610 | A | 8/1996 | Russell et al. |
| 5,573,012 | A | 11/1996 | McEwan |
| 5,575,790 | A | 11/1996 | Chen et al. |
| 5,582,616 | A | 12/1996 | Bolduc et al. |
| 5,620,445 | A | 4/1997 | Brosnahan et al. |
| 5,620,449 | A | 4/1997 | Faccioli et al. |
| 5,626,579 | A | 5/1997 | Muschler et al. |
| 5,626,613 | A | 5/1997 | Schmieding |
| 5,632,744 | A | 5/1997 | Campbell, Jr. |
| 5,659,217 | A | 8/1997 | Petersen |
| 5,662,683 | A | 9/1997 | Kay |
| 5,672,175 | A | 9/1997 | Martin |
| 5,672,177 | A | 9/1997 | Seldin |
| 5,700,263 | A | 12/1997 | Schendel |
| 5,704,938 | A | 1/1998 | Staehlin et al. |
| 5,704,939 | A | 1/1998 | Justin |
| 5,720,746 | A | 2/1998 | Soubeiran |
| 5,743,910 | A | 4/1998 | Bays et al. |
| 5,762,599 | A | 6/1998 | Sohn |
| 5,771,903 | A | 6/1998 | Jakobsson |
| 5,810,815 | A | 9/1998 | Morales |
| 5,827,286 | A | 10/1998 | Incavo et al. |
| 5,830,221 | A | 11/1998 | Stein et al. |
| 5,879,375 | A | 3/1999 | Larson, Jr. et al. |
| 5,902,304 | A | 5/1999 | Walker et al. |
| 5,935,127 | A | 8/1999 | Border |
| 5,945,762 | A | 8/1999 | Chen et al. |
| 5,961,553 | A | 10/1999 | Coty et al. |
| 5,976,138 | A | 11/1999 | Baumgart et al. |
| 5,979,456 | A | 11/1999 | Magovern |
| 6,022,349 | A | 2/2000 | McLeod et al. |
| 6,033,412 | A | 3/2000 | Losken et al. |
| 6,034,296 | A | 3/2000 | Elvin et al. |
| 6,102,922 | A | 8/2000 | Jakobsson et al. |
| 6,106,525 | A | 8/2000 | Sachse |
| 6,126,660 | A | 10/2000 | Dietz |
| 6,126,661 | A | 10/2000 | Faccioli et al. |
| 6,138,681 | A | 10/2000 | Chen et al. |
| 6,139,316 | A | 10/2000 | Sachdeva et al. |
| 6,162,223 | A | 12/2000 | Orsak et al. |
| 6,183,476 | B1 | 2/2001 | Gerhardt et al. |
| 6,200,317 | B1 | 3/2001 | Aalsma et al. |
| 6,234,956 | B1 | 5/2001 | He et al. |
| 6,241,730 | B1 | 6/2001 | Alby |
| 6,245,075 | B1 | 6/2001 | Betz et al. |
| 6,315,784 | B1 | 11/2001 | Djurovic |
| 6,319,255 | B1 | 11/2001 | Grundei et al. |
| 6,331,744 | B1 | 12/2001 | Chen et al. |
| 6,336,929 | B1 | 1/2002 | Justin |
| 6,343,568 | B1 | 2/2002 | McClasky |
| 6,358,283 | B1 | 3/2002 | Hogfors et al. |
| 6,375,682 | B1 | 4/2002 | Fleischmann et al. |
| 6,389,187 | B1 | 5/2002 | Greenaway et al. |
| 6,400,980 | B1 | 6/2002 | Lemelson |
| 6,402,753 | B1 | 6/2002 | Cole et al. |
| 6,409,175 | B1 | 6/2002 | Evans et al. |
| 6,416,516 | B1 | 7/2002 | Stauch et al. |
| 6,499,907 | B1 | 12/2002 | Baur |
| 6,500,110 | B1 | 12/2002 | Davey et al. |
| 6,508,820 | B2 | 1/2003 | Bales |
| 6,510,345 | B1 | 1/2003 | Van Bentem |
| 6,537,196 | B1 | 3/2003 | Creighton, IV et al. |
| 6,554,831 | B1 | 4/2003 | Rivard et al. |
| 6,565,573 | B1 | 5/2003 | Ferrante et al. |
| 6,565,576 | B1 | 5/2003 | Stauch et al. |
| 6,582,313 | B2 | 6/2003 | Perrow |
| 6,583,630 | B2 | 6/2003 | Mendes et al. |
| 6,616,669 | B2 | 9/2003 | Ogilvie et al. |
| 6,626,917 | B1 | 9/2003 | Craig |
| 6,656,135 | B2 | 12/2003 | Zogbi et al. |
| 6,656,194 | B1 | 12/2003 | Gannoe et al. |
| 6,667,725 | B1 | 12/2003 | Simons et al. |
| 6,673,079 | B1 | 1/2004 | Kane |
| 6,702,816 | B2 | 3/2004 | Buhler |
| 6,706,042 | B2 | 3/2004 | Taylor |
| 6,709,293 | B2 | 3/2004 | Mori et al. |
| 6,730,087 | B1 | 5/2004 | Butsch |
| 6,761,503 | B2 | 7/2004 | Breese |
| 6,769,499 | B2 | 8/2004 | Cargill et al. |
| 6,789,442 | B2 | 9/2004 | Forch |
| 6,796,984 | B2 | 9/2004 | Soubeiran |
| 6,802,844 | B2 | 10/2004 | Ferree |
| 6,809,434 | B1 | 10/2004 | Duncan et al. |
| 6,835,207 | B2 | 12/2004 | Zacouto et al. |
| 6,852,113 | B2 | 2/2005 | Nathanson et al. |
| 6,918,838 | B2 | 7/2005 | Schwarzler et al. |
| 6,918,910 | B2 | 7/2005 | Smith et al. |
| 6,921,400 | B2 | 7/2005 | Sohngen |
| 6,923,951 | B2 | 8/2005 | Contag et al. |
| 6,971,143 | B2 | 12/2005 | Domroese |
| 7,001,346 | B2 | 2/2006 | White |

(56) References Cited

U.S. PATENT DOCUMENTS 7,008,425 B2 3/2006 Phillips
7,011,658 B2 3/2006 Young
7,029,472 B1 4/2006 Fortin
7,029,475 B2 4/2006 Panjabi
7,041,105 B2 5/2006 Michelson
7,060,080 B2 6/2006 Bachmann
7,063,706 B2 6/2006 Wittenstein
7,105,029 B2 9/2006 Doubler et al.
7,105,968 B2 9/2006 Nissen
7,114,501 B2 10/2006 Johnson et al.
7,115,129 B2 10/2006 Heggeness
7,135,022 B2 11/2006 Kosashvili et al.
7,160,312 B2 1/2007 Saadat
7,163,538 B2 1/2007 Altarac et al.
7,189,005 B2 3/2007 Ward
7,191,007 B2 3/2007 Desai et al.
7,218,232 B2 5/2007 DiSilvestro et al.
7,238,191 B2 7/2007 Bachmann
7,241,300 B2 7/2007 Sharkawy et al.
7,243,719 B2 7/2007 Baron et al.
7,255,682 B1 8/2007 Bartol, Jr. et al.
7,282,023 B2 10/2007 Frering
7,285,087 B2 10/2007 Moaddeb et al.
7,302,015 B2 11/2007 Kim et al.
7,302,858 B2 12/2007 Walsh et al.
7,314,443 B2 1/2008 Jordan et al.
7,333,013 B2 2/2008 Berger
7,357,037 B2 4/2008 Hnat et al.
7,357,635 B2 4/2008 Belfor et al.
7,360,542 B2 4/2008 Nelson et al.
7,390,007 B2 6/2008 Helms et al.
7,390,294 B2 6/2008 Hassler, Jr.
7,402,134 B2 7/2008 Moaddeb et al.
7,402,176 B2 7/2008 Malek
7,429,259 B2 9/2008 Cadeddu et al.
7,445,010 B2 11/2008 Kugler et al.
7,458,981 B2 12/2008 Fielding et al.
7,485,149 B1 2/2009 White
7,489,495 B2 2/2009 Stevenson
7,530,981 B2 5/2009 Kutsenko
7,531,002 B2 5/2009 Sutton et al.
7,553,298 B2 6/2009 Hunt et al.
7,561,916 B2 7/2009 Hunt et al.
7,611,526 B2 11/2009 Carl et al.
7,618,435 B2 11/2009 Opolski
7,658,754 B2 2/2010 Zhang et al.
7,666,184 B2 2/2010 Stauch
7,666,210 B2 2/2010 Franck et al.
7,678,136 B2 3/2010 Doubler et al.
7,678,139 B2 3/2010 Garamszegi et al.
7,708,737 B2 5/2010 Kraft et al.
7,708,762 B2 5/2010 McCarthy et al.
7,727,143 B2 6/2010 Birk et al.
7,753,913 B2 7/2010 Szakelyhidi, Jr. et al.
7,753,915 B1 7/2010 Eksler et al.
7,762,998 B2 7/2010 Birk et al.
7,763,080 B2 7/2010 Southworth
7,766,855 B2 8/2010 Miethke
7,775,215 B2 8/2010 Hassler, Jr. et al.
7,776,068 B2 8/2010 Ainsworth et al.
7,776,075 B2 8/2010 Bruneau et al.
7,787,958 B2 8/2010 Stevenson
7,794,476 B2 9/2010 Wisnewski
7,811,328 B2 10/2010 Molz, IV et al.
7,835,779 B2 11/2010 Anderson et al.
7,837,691 B2 11/2010 Cordes et al.
7,862,586 B2 1/2011 Malek
7,867,235 B2 1/2011 Fell et al.
7,875,033 B2 1/2011 Richter et al.
7,901,381 B2 3/2011 Birk et al.
7,909,852 B2 3/2011 Boomer et al.
7,918,844 B2 4/2011 Byrum et al.
7,938,841 B2 5/2011 Sharkawy et al.
7,985,256 B2 7/2011 Grotz et al.
7,988,709 B2 8/2011 Clark et al.
8,002,809 B2 8/2011 Baynham
8,011,308 B2 9/2011 Picchio
8,034,080 B2 10/2011 Malandain et al.
8,043,299 B2 10/2011 Conway
8,043,338 B2 10/2011 Dant
8,057,473 B2 11/2011 Orsak et al.
8,057,513 B2 11/2011 Kohm et al.
8,083,741 B2 12/2011 Morgan et al.
8,092,499 B1 1/2012 Roth
8,095,317 B2 1/2012 Ekseth et al.
8,105,360 B1 1/2012 Connor
8,114,158 B2 2/2012 Carl et al.
8,123,805 B2 2/2012 Makower et al.
8,133,280 B2 3/2012 Voellmicke et al.
8,147,549 B2 4/2012 Metcalf, Jr. et al.
8,162,897 B2 4/2012 Byrum
8,162,979 B2 4/2012 Sachs et al.
8,177,789 B2 5/2012 Magill et al.
8,197,490 B2 6/2012 Pool et al.
8,211,149 B2 7/2012 Justis
8,211,151 B2 7/2012 Schwab et al.
8,221,420 B2 7/2012 Keller
8,226,690 B2 7/2012 Altarac et al.
8,236,002 B2 8/2012 Fortin et al.
8,241,331 B2 8/2012 Arnin
8,246,630 B2 8/2012 Manzi et al.
8,252,063 B2 8/2012 Stauch
8,267,969 B2 9/2012 Altarac et al.
8,278,941 B2 10/2012 Kroh et al.
8,282,671 B2 10/2012 Connor
8,323,290 B2 12/2012 Metzger et al.
8,357,182 B2 1/2013 Seme
8,366,628 B2 2/2013 Denker et al.
8,372,078 B2 2/2013 Collazo
8,386,018 B2 2/2013 Stauch et al.
8,394,124 B2 3/2013 Biyani
8,403,958 B2 3/2013 Schwab
8,414,584 B2 4/2013 Brigido
8,425,608 B2 4/2013 Dewey et al.
8,435,268 B2 5/2013 Thompson et al.
8,439,926 B2 5/2013 Bojarski et al.
8,444,693 B2 5/2013 Reiley
8,469,908 B2 6/2013 Asfora
8,470,004 B2 6/2013 Reiley
8,486,070 B2 7/2013 Morgan et al.
8,486,076 B2 7/2013 Chavarria et al.
8,486,147 B2 7/2013 De Villiers et al.
8,494,805 B2 7/2013 Roche et al.
8,496,662 B2 7/2013 Novak et al.
8,518,062 B2 8/2013 Cole et al.
8,523,866 B2 9/2013 Sidebotham et al.
8,529,474 B2 9/2013 Gupta et al.
8,529,606 B2 9/2013 Alamin et al.
8,529,607 B2 9/2013 Alamin et al.
8,556,901 B2 10/2013 Anthony et al.
8,556,911 B2 10/2013 Mehta et al.
8,556,975 B2 10/2013 Ciupik et al.
8,562,653 B2 10/2013 Alamin et al.
8,568,457 B2 10/2013 Hunziker
8,579,979 B2 11/2013 Edie et al.
8,585,595 B2 11/2013 Heilman
8,585,740 B1 11/2013 Ross et al.
8,591,549 B2 11/2013 Lange
8,591,553 B2 11/2013 Eisermann et al.
8,613,758 B2 12/2013 Linares
8,617,220 B2 12/2013 Skaggs
8,623,036 B2 1/2014 Harrison et al.
8,632,544 B2 1/2014 Haaja et al.
8,632,548 B2 1/2014 Soubeiran
8,632,563 B2 1/2014 Nagase et al.
8,636,771 B2 1/2014 Butler et al.
8,636,802 B2 1/2014 Serhan et al.
8,641,719 B2 2/2014 Gephart et al.
8,641,723 B2 2/2014 Connor
8,657,856 B2 2/2014 Gephart et al.
8,663,285 B2 3/2014 Dall et al.
8,663,287 B2 3/2014 Butler et al.
8,668,719 B2 3/2014 Alamin et al.
8,709,090 B2 4/2014 Makower et al.

(56) References Cited

U.S. PATENT DOCUMENTS

| | | | |
|---|---|---|---|
| 8,758,347 | B2 | 6/2014 | Weiner et al. |
| 8,758,355 | B2 | 6/2014 | Fisher et al. |
| 8,771,272 | B2 | 7/2014 | LeCronier et al. |
| 8,777,947 | B2 | 7/2014 | Zahrly et al. |
| 8,777,995 | B2 | 7/2014 | McClintock et al. |
| 8,790,343 | B2 | 7/2014 | McClellan et al. |
| 8,790,409 | B2 | 7/2014 | Van den Heuvel et al. |
| 8,828,058 | B2 | 9/2014 | Elsebaie et al. |
| 8,828,087 | B2 | 9/2014 | Stone et al. |
| 8,840,651 | B2 | 9/2014 | Reiley |
| 8,870,881 | B2 | 10/2014 | Rezach et al. |
| 8,870,959 | B2 | 10/2014 | Arnin |
| 8,915,915 | B2 | 12/2014 | Harrison et al. |
| 8,915,917 | B2 | 12/2014 | Doherty et al. |
| 8,920,422 | B2 | 12/2014 | Homeier et al. |
| 8,945,188 | B2 | 2/2015 | Rezach et al. |
| 8,961,521 | B2 | 2/2015 | Keefer et al. |
| 8,961,567 | B2 | 2/2015 | Hunziker |
| 8,968,402 | B2 | 3/2015 | Myers et al. |
| 8,992,527 | B2 | 3/2015 | Guichet |
| 9,022,917 | B2 | 5/2015 | Kasic et al. |
| 9,044,218 | B2 | 6/2015 | Young |
| 9,060,810 | B2 | 6/2015 | Kercher et al. |
| 9,078,703 | B2 | 7/2015 | Arnin |
| 2002/0050112 | A1 | 5/2002 | Koch et al. |
| 2002/0072758 | A1 | 6/2002 | Reo et al. |
| 2002/0164905 | A1 | 11/2002 | Bryant |
| 2003/0040671 | A1 | 2/2003 | Somogyi et al. |
| 2003/0144669 | A1 | 7/2003 | Robinson |
| 2003/0220643 | A1 | 11/2003 | Ferree |
| 2003/0220644 | A1 | 11/2003 | Thelen et al. |
| 2004/0011137 | A1 | 1/2004 | Hnat et al. |
| 2004/0011365 | A1 | 1/2004 | Govari et al. |
| 2004/0019353 | A1 | 1/2004 | Freid et al. |
| 2004/0023623 | A1 | 2/2004 | Stauch et al. |
| 2004/0055610 | A1 | 3/2004 | Forsell |
| 2004/0133219 | A1 | 7/2004 | Forsell |
| 2004/0138725 | A1 | 7/2004 | Forsell |
| 2004/0193266 | A1 | 9/2004 | Meyer |
| 2005/0034705 | A1 | 2/2005 | McClendon |
| 2005/0049617 | A1 | 3/2005 | Chatlynne et al. |
| 2005/0065529 | A1 | 3/2005 | Liu et al. |
| 2005/0090823 | A1 | 4/2005 | Bartimus |
| 2005/0159754 | A1 | 7/2005 | Odrich |
| 2005/0234448 | A1 | 10/2005 | McCarthy |
| 2005/0234462 | A1 | 10/2005 | Hershberger |
| 2005/0246034 | A1 | 11/2005 | Soubeiran |
| 2005/0261779 | A1 | 11/2005 | Meyer |
| 2005/0272976 | A1 | 12/2005 | Tanaka et al. |
| 2006/0004459 | A1 | 1/2006 | Hazebrouck et al. |
| 2006/0009767 | A1 | 1/2006 | Kiester |
| 2006/0036259 | A1 | 2/2006 | Carl et al. |
| 2006/0036323 | A1 | 2/2006 | Carl et al. |
| 2006/0036324 | A1 | 2/2006 | Sachs et al. |
| 2006/0047282 | A1 | 3/2006 | Gordon |
| 2006/0058792 | A1 | 3/2006 | Hynes |
| 2006/0069447 | A1 | 3/2006 | DiSilvestro et al. |
| 2006/0074448 | A1 | 4/2006 | Harrison et al. |
| 2006/0079897 | A1 | 4/2006 | Harrison et al. |
| 2006/0136062 | A1 | 6/2006 | DiNello et al. |
| 2006/0142767 | A1 | 6/2006 | Green et al. |
| 2006/0155279 | A1 | 7/2006 | Ogilvie |
| 2006/0195087 | A1 | 8/2006 | Sacher et al. |
| 2006/0195088 | A1 | 8/2006 | Sacher et al. |
| 2006/0200134 | A1 | 9/2006 | Freid et al. |
| 2006/0204156 | A1 | 9/2006 | Takehara et al. |
| 2006/0235299 | A1 | 10/2006 | Martinelli |
| 2006/0235424 | A1 | 10/2006 | Vitale et al. |
| 2006/0241746 | A1 | 10/2006 | Shaoulian et al. |
| 2006/0241767 | A1 | 10/2006 | Doty |
| 2006/0249914 | A1 | 11/2006 | Dulin |
| 2006/0271107 | A1 | 11/2006 | Harrison et al. |
| 2006/0282073 | A1 | 12/2006 | Simanovsky |
| 2006/0293683 | A1 | 12/2006 | Stauch |
| 2007/0010814 | A1 | 1/2007 | Stauch |
| 2007/0010887 | A1 | 1/2007 | Williams et al. |
| 2007/0021644 | A1 | 1/2007 | Woolson et al. |
| 2007/0031131 | A1 | 2/2007 | Griffitts |
| 2007/0043376 | A1 | 2/2007 | Leatherbury et al. |
| 2007/0050030 | A1 | 3/2007 | Kim |
| 2007/0118215 | A1 | 5/2007 | Moaddeb |
| 2007/0161984 | A1 | 7/2007 | Cresina et al. |
| 2007/0173837 | A1 | 7/2007 | Chan et al. |
| 2007/0179493 | A1 | 8/2007 | Kim |
| 2007/0185374 | A1 | 8/2007 | Kick et al. |
| 2007/0233098 | A1 | 10/2007 | Mastrorio et al. |
| 2007/0239159 | A1 | 10/2007 | Altarac et al. |
| 2007/0239161 | A1 | 10/2007 | Giger et al. |
| 2007/0255088 | A1 | 11/2007 | Jacobson et al. |
| 2007/0270803 | A1 | 11/2007 | Giger et al. |
| 2007/0276368 | A1 | 11/2007 | Trieu et al. |
| 2007/0276369 | A1 | 11/2007 | Allard et al. |
| 2007/0276373 | A1 | 11/2007 | Malandain |
| 2007/0276378 | A1 | 11/2007 | Harrison et al. |
| 2007/0276493 | A1 | 11/2007 | Malandain et al. |
| 2007/0288024 | A1 | 12/2007 | Gollogly |
| 2007/0288183 | A1 | 12/2007 | Bulkes et al. |
| 2008/0009792 | A1 | 1/2008 | Henniges et al. |
| 2008/0015577 | A1 | 1/2008 | Loeb |
| 2008/0021454 | A1 | 1/2008 | Chao et al. |
| 2008/0021455 | A1 | 1/2008 | Chao et al. |
| 2008/0021456 | A1 | 1/2008 | Gupta et al. |
| 2008/0027436 | A1 | 1/2008 | Cournoyer et al. |
| 2008/0033431 | A1 | 2/2008 | Jung et al. |
| 2008/0033436 | A1 | 2/2008 | Song et al. |
| 2008/0051784 | A1 | 2/2008 | Gollogly |
| 2008/0082118 | A1 | 4/2008 | Edidin et al. |
| 2008/0086128 | A1 | 4/2008 | Lewis |
| 2008/0097487 | A1 | 4/2008 | Pool et al. |
| 2008/0097496 | A1 | 4/2008 | Chang et al. |
| 2008/0108995 | A1 | 5/2008 | Conway et al. |
| 2008/0161933 | A1 | 7/2008 | Grotz et al. |
| 2008/0167685 | A1 | 7/2008 | Allard et al. |
| 2008/0172063 | A1 | 7/2008 | Taylor |
| 2008/0177319 | A1 | 7/2008 | Schwab |
| 2008/0177326 | A1 | 7/2008 | Thompson |
| 2008/0190237 | A1 | 8/2008 | Radinger et al. |
| 2008/0228186 | A1 | 9/2008 | Gall et al. |
| 2008/0255615 | A1 | 10/2008 | Vittur et al. |
| 2008/0272928 | A1 | 11/2008 | Shuster |
| 2008/0275557 | A1 | 11/2008 | Makower et al. |
| 2009/0030462 | A1 | 1/2009 | Buttermann |
| 2009/0076597 | A1 | 3/2009 | Dahlgren et al. |
| 2009/0082815 | A1 | 3/2009 | Zylber et al. |
| 2009/0088803 | A1 | 4/2009 | Justis et al. |
| 2009/0093820 | A1 | 4/2009 | Trieu et al. |
| 2009/0093890 | A1 | 4/2009 | Gelbart |
| 2009/0112263 | A1 | 4/2009 | Pool et al. |
| 2009/0163780 | A1 | 6/2009 | Tieu |
| 2009/0171356 | A1 | 7/2009 | Klett |
| 2009/0192514 | A1 | 7/2009 | Feinberg et al. |
| 2009/0198144 | A1 | 8/2009 | Phillips et al. |
| 2009/0216113 | A1 | 8/2009 | Meier et al. |
| 2009/0275984 | A1 | 11/2009 | Kim et al. |
| 2010/0004654 | A1 | 1/2010 | Schmitz et al. |
| 2010/0057127 | A1 | 3/2010 | McGuire et al. |
| 2010/0094306 | A1 | 4/2010 | Chang et al. |
| 2010/0100185 | A1 | 4/2010 | Trieu et al. |
| 2010/0106192 | A1 | 4/2010 | Barry |
| 2010/0114322 | A1 | 5/2010 | Clifford et al. |
| 2010/0130941 | A1 | 5/2010 | Conlon et al. |
| 2010/0137872 | A1 | 6/2010 | Kam et al. |
| 2010/0145449 | A1 | 6/2010 | Makower et al. |
| 2010/0145462 | A1 | 6/2010 | Ainsworth et al. |
| 2010/0168751 | A1 | 7/2010 | Anderson et al. |
| 2010/0249782 | A1 | 9/2010 | Durham |
| 2010/0256626 | A1 | 10/2010 | Muller et al. |
| 2010/0262239 | A1 | 10/2010 | Boyden et al. |
| 2010/0318129 | A1 | 12/2010 | Seme et al. |
| 2010/0331883 | A1 | 12/2010 | Schmitz et al. |
| 2011/0004076 | A1 | 1/2011 | Janna et al. |
| 2011/0057756 | A1 | 3/2011 | Marinescu et al. |
| 2011/0066188 | A1 | 3/2011 | Seme et al. |
| 2011/0098748 | A1 | 4/2011 | Jangra |

(56) References Cited

U.S. PATENT DOCUMENTS

| | | | |
|---|---|---|---|
| 2011/0152725 | A1 | 6/2011 | Demir et al. |
| 2011/0196435 | A1 | 8/2011 | Forsell |
| 2011/0202138 | A1 | 8/2011 | Shenoy et al. |
| 2011/0238126 | A1 | 9/2011 | Soubeiran |
| 2011/0257655 | A1 | 10/2011 | Copf, Jr. |
| 2011/0284014 | A1 | 11/2011 | Cadeddu et al. |
| 2012/0019341 | A1 | 1/2012 | Gabay et al. |
| 2012/0019342 | A1 | 1/2012 | Gabay et al. |
| 2012/0053633 | A1 | 3/2012 | Stauch |
| 2012/0088953 | A1 | 4/2012 | King |
| 2012/0109207 | A1 | 5/2012 | Trieu |
| 2012/0116535 | A1 | 5/2012 | Ratron et al. |
| 2012/0158061 | A1 | 6/2012 | Koch et al. |
| 2012/0172883 | A1 | 7/2012 | Sayago |
| 2012/0179215 | A1 | 7/2012 | Soubeiran |
| 2012/0221106 | A1 | 8/2012 | Makower et al. |
| 2012/0271353 | A1 | 10/2012 | Barry |
| 2012/0296234 | A1 | 11/2012 | Wilhelm et al. |
| 2012/0329882 | A1 | 12/2012 | Messersmith et al. |
| 2013/0013066 | A1 | 1/2013 | Landry et al. |
| 2013/0072932 | A1 | 3/2013 | Stauch |
| 2013/0123847 | A1 | 5/2013 | Anderson et al. |
| 2013/0138017 | A1 | 5/2013 | Jundt et al. |
| 2013/0138154 | A1 | 5/2013 | Reiley |
| 2013/0150863 | A1 | 6/2013 | Baumgartner |
| 2013/0150889 | A1 | 6/2013 | Fening et al. |
| 2013/0178903 | A1 | 7/2013 | Abdou |
| 2013/0211521 | A1 | 8/2013 | Shenoy et al. |
| 2013/0245692 | A1 | 9/2013 | Hayes et al. |
| 2013/0253344 | A1 | 9/2013 | Griswold et al. |
| 2013/0253587 | A1 | 9/2013 | Carls et al. |
| 2013/0261672 | A1 | 10/2013 | Horvath |
| 2013/0296863 | A1 | 11/2013 | Globerman et al. |
| 2013/0296864 | A1 | 11/2013 | Burley et al. |
| 2013/0296940 | A1 | 11/2013 | Northcutt et al. |
| 2013/0325006 | A1 | 12/2013 | Michelinie et al. |
| 2013/0325071 | A1 | 12/2013 | Niemiec et al. |
| 2014/0005788 | A1 | 1/2014 | Haaja et al. |
| 2014/0025172 | A1 | 1/2014 | Lucas et al. |
| 2014/0052134 | A1 | 2/2014 | Orisek |
| 2014/0058392 | A1 | 2/2014 | Mueckter et al. |
| 2014/0058450 | A1 | 2/2014 | Arlet |
| 2014/0066987 | A1 | 3/2014 | Hestad et al. |
| 2014/0088715 | A1 | 3/2014 | Ciupik |
| 2014/0128920 | A1 | 5/2014 | Kantelhardt |
| 2014/0163664 | A1 | 6/2014 | Goldsmith |
| 2014/0236234 | A1 | 8/2014 | Kroll et al. |
| 2014/0236311 | A1 | 8/2014 | Vicatos et al. |
| 2014/0257412 | A1 | 9/2014 | Patty et al. |
| 2014/0277446 | A1 | 9/2014 | Clifford et al. |
| 2014/0296918 | A1 | 10/2014 | Fening et al. |
| 2014/0303538 | A1 | 10/2014 | Baym et al. |
| 2014/0303539 | A1 | 10/2014 | Baym et al. |
| 2014/0358150 | A1 | 12/2014 | Kaufman et al. |
| 2015/0105782 | A1 | 4/2015 | D'Lima et al. |
| 2015/0105824 | A1 | 4/2015 | Moskowitz et al. |

FOREIGN PATENT DOCUMENTS

| | | | |
|---|---|---|---|
| DE | 1541262 | A1 | 6/1969 |
| DE | 8515687 | U1 | 12/1985 |
| DE | 19626230 | A1 | 1/1998 |
| DE | 19745654 | A1 | 4/1999 |
| DE | 102005045070 | A1 | 4/2007 |
| EP | 0663184 | A1 | 7/1995 |
| EP | 1905388 | A1 | 4/2008 |
| FR | 2901991 | A1 | 12/2007 |
| FR | 2900563 | B1 | 8/2008 |
| FR | 2892617 | B1 | 9/2008 |
| FR | 2916622 | B1 | 9/2009 |
| FR | 2961386 | B1 | 12/2011 |
| JP | H0956736 | | 3/1997 |
| JP | 2002500063 | A | 1/2002 |
| WO | WO1998044858 | A1 | 10/1998 |
| WO | WO1999051160 | A1 | 10/1999 |
| WO | WO2001024697 | A1 | 4/2001 |
| WO | WO2001045485 | A3 | 6/2001 |
| WO | WO2001045487 | A2 | 6/2001 |
| WO | WO2001067973 | A2 | 9/2001 |
| WO | WO2001078614 | A1 | 10/2001 |
| WO | WO2007013059 | A3 | 2/2007 |
| WO | WO2007015239 | A3 | 2/2007 |
| WO | WO2011116158 | A3 | 9/2011 |
| WO | WO2013119528 | A1 | 8/2013 |
| WO | WO2014040013 | A1 | 3/2014 |

OTHER PUBLICATIONS

Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™ System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

(56) References Cited

OTHER PUBLICATIONS

Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", Spine, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.
INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment.", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.

(56) References Cited

OTHER PUBLICATIONS

Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.
Zheng et al., "Force and torque characteristics for magnetically driven blood pump.", Journal of Magnetism and Magnetic Materials, 2002, pp. 292-302, 241, No. 2.

ADJUSTABLE TETHER IMPLANT

CROSS-REFERENCE TO RELATED APPLICATIONS

This application claims priority to U.S. Provisional Application No. 63/378,787, filed on Oct. 7, 2022.

TECHNICAL FIELD

The subject matter described herein relates generally to adjustable implants, including adjustable bone anchor(s) tethered to fixed bone anchor(s).

BACKGROUND

Hemiepiphysiodesis is a medical procedure to correct skeletal deformities using an implant to shape bone growth in a particular direction. Typical treatment methods include physical tethering utilizing non-adjustable plates and screws, such that correction of a skeletal deformity is planned around a patient's natural growth. If the procedure is timed incorrectly, the existing deformity may not be properly corrected, or a new deformity could be created due to over correction. Embodiments of the present disclosure aim to address these problems with hemiephysiodesis, as well as other problems generally with adjustable implants.

SUMMARY

All aspects, examples and features mentioned below can be combined in any technically possible way.

An aspect of the disclosure provides an implant system, including: a tether having a first end opposite a second end; a fixed bone anchor configured to couple to the first end of the tether; and an adjustable bone anchor configured to couple to the second end of the tether. The adjustable bone anchor includes: a housing extending between a distal end and a proximal end of the adjustable bone anchor; a driver disposed within the housing and configured to drive rotational motion; an output shaft extending proximally from the driver; a screw cap disposed at the proximal end of the adjustable bone anchor; and a clamping mechanism having a lower portion configured to rotatably engage the output shaft, and an upper portion configured to couple to an inner surface of the screw cap. The lower portion of the clamping mechanism is configured to translate within the housing in response to rotation by the driver relative to the lower portion. The clamping mechanism is configured to secure the adjustable bone anchor to the tether.

Another aspect of the disclosure includes any of the preceding aspects, and an implant system including: a tether having a first end and a second end; a fixed bone anchor configured to couple to bone and the first end of the tether; and an adjustable bone anchor configured to couple to bone and the second end of the tether. The adjustable bone anchor includes: a housing extending between a distal end and a proximal end of the adjustable bone anchor; a driver disposed within the housing and configured to drive rotational motion; an output shaft extending proximally from the driver; and a locking mechanism disposed within the housing. The locking mechanism includes a distal portion with proximal facing teeth, and a proximal portion that includes a spool and a plurality of teeth extending distally therefrom. The distal portion of the locking mechanism is configured to rotatably engage with the output shaft and to translate in response to rotation of the output shaft. A spool extends proximally from the proximal portion of the locking mechanism. The second end of the tether is configured to wrap around the spool.

Another aspect of the disclosure includes any of the preceding aspects, and an implant system including: a tether having a first end and a second end; a fixed bone anchor configured to couple to the first end of the tether; and an adjustable bone anchor configured to couple to the second end of the tether. The adjustable bone anchor includes: a housing extending between a distal end and a proximal end of the adjustable bone anchor; a driver disposed within the housing, and configured to drive rotational motion; a gear system coupled to a proximal end of the driver; and an output member coupled to the gear system, the output member including a spool configured to receive the tether.

Another aspect of the disclosure includes any of the preceding aspects, and an implant system, including: a fixed bone anchor; a tether having a first end coupled to the fixed bone anchor; and an adjustable bone anchor coupled to a second end of the tether. The adjustable bone anchor includes: a housing extending between a distal end and a proximal end of the adjustable bone anchor; a driver disposed within the housing; an output member configured to be rotated by the driver, the output member including an internally threaded portion; a connector that includes a distal portion disposed within and in threaded engagement with the output member, and a proximal portion coupled to the second end of the tether. The connector is configured to translate relative to the output member to adjust the tether. The adjustable bone anchor further includes a first plate coupled to the proximal end of the adjustable bone anchor, the plate including a first aperture configured to receive the proximal portion of the connector; and a first attachment feature configured to couple to the tether at a first point between the first end and the second end thereof.

Another aspect of the disclosure includes any of the preceding aspects, and an implant system including: a tether; a first bone anchor; and a second bone anchor. The second bone anchor is configured to be transcutaneously and post-operatively actuated through intact skin to slacken or tighten the tether, when the tether connects the first bone anchor and the second bone anchor.

Another aspect of the disclosure includes any of the preceding aspects, and a method including slackening or tightening a growth-plate-spanning tether coupled to the first anchor by post-operatively and non-invasively actuating an actuator of a first anchor implanted in a patient.

Two or more aspects described in this disclosure, including those described in this summary section, may be combined to form implementations not specifically described herein.

The details of one or more implementations are set forth in the accompanying drawings and the description below. Other features, objects and advantages will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

Figure 1:
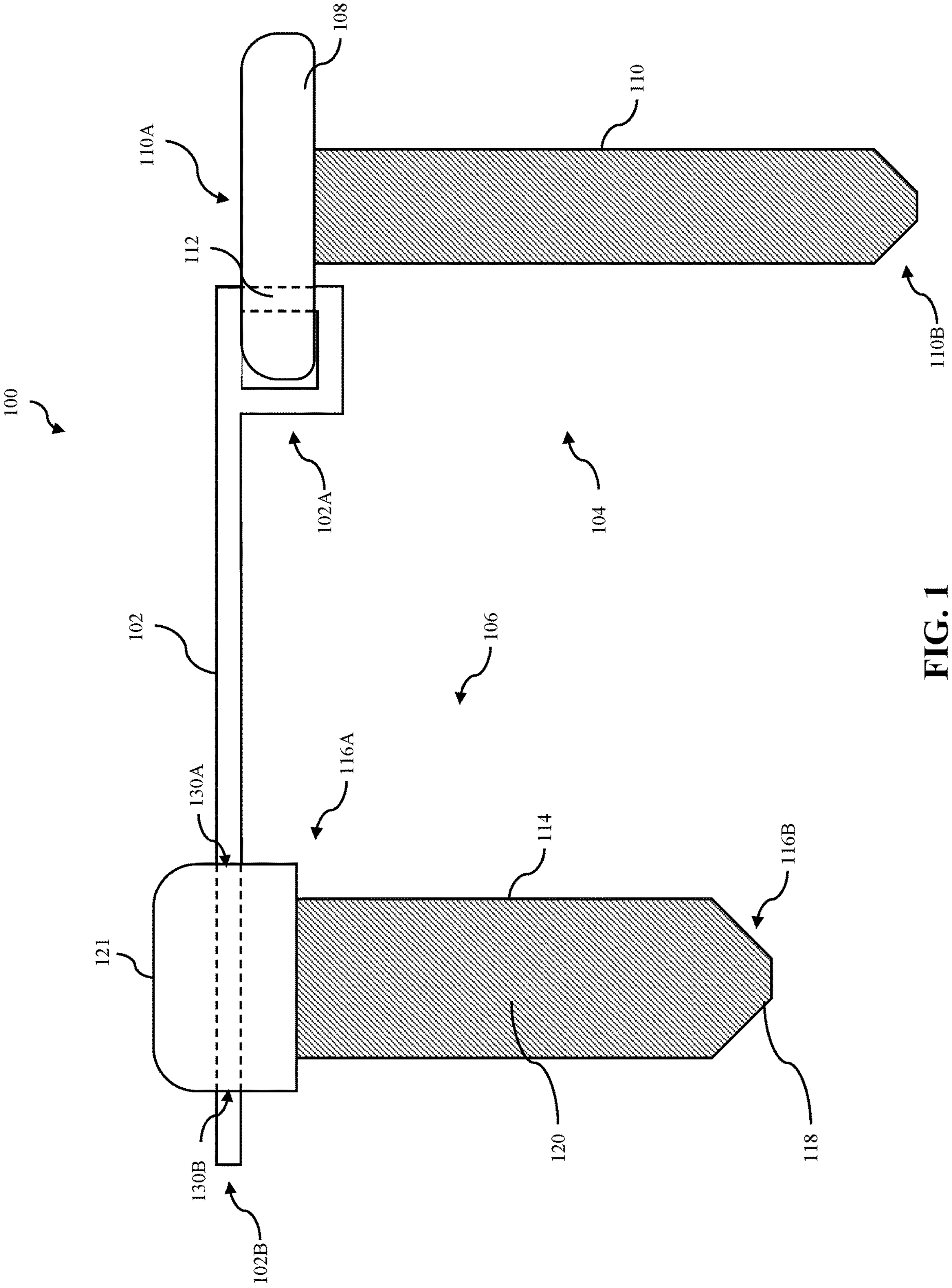
FIG. 1 illustrates an implant system according to a first embodiment.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

The present disclosure describes various embodiments of an adjustable implant system, such embodiments including a tether having a first end opposite a second end, a first bone anchor coupled to the first end of the tether, and a second bone anchor coupled to the second end of the tether. In various embodiments, the first bone anchor may be a fixed bone anchor and the second bone anchor may be an adjustable bone anchor. The adjustable bone anchor may be configured to increase or decrease tension in the tether using one or more mechanisms discussed herein. The adjustable implant system may be configured to be externally controlled by an external adjustment device and may therefore be non-invasively adjustable in such embodiments.

In some embodiments, an adjustable bone anchor includes a clamping mechanism configured to engage or disengage a tether extending therethrough. In other embodiments, an adjustable bone anchor includes a spool configured to receive a portion of the tether thereon, increasing or decreasing tension in the tether when in a locked or unlocked position, respectively.

In some embodiments, an implant system includes a tether, a first bone anchor, and a second bone anchor. The tether may include one or more biocompatible materials, such as polyethylene. The first and second bone anchor may include one or more biocompatible materials, such as titanium.

In some embodiments, an implant system includes a tether, a first bone anchor, and a second bone anchor. The second bone anchor is configured to be transcutaneously actuated post-operatively through intact skin to slacken or tighten the tether, when the tether connects the first bone anchor and the second bone anchor. The second bone anchor may include a clamp configured to grasp the tether, and to release the grasp on the tether in response to sufficient transcutaneous actuation. As used herein, transcutaneous actuation may be considered sufficient when a first portion of the clamp is separated from a second portion of the clamp such that a gap between the first and second portions allow the tether to pass through the gap unencumbered. The second bone anchor may further include a spool configured to hold a wound section of the tether, and to unwind in response to sufficient transcutaneous actuation. As used herein, transcutaneous actuation may be considered sufficient when a first portion of a locking mechanism is separated from a second portion of the locking mechanism such that the spool freely rotates about a rotational axis to unwind the tether.

In some embodiments, the present disclosure provides a method of slackening a growth-plate-spanning tether coupled to a first anchor by post-operatively and non-invasively actuating an actuator of the first anchor implanted in a patient. The growth plate of the patient may be active. Actuating the actuator of the first anchor may include causing a clamp to release the tether, thereby slackening the tether. Actuating the actuator of the first anchor may include causing a spool to unspool the tether, thereby slackening the tether. Actuating the actuator of the first anchor may occur transcutaneously through intact skin. The method may further include implanting the first anchor in the patient, implanting a second anchor in the patient, and coupling the first anchor and the second anchor with the tether, such that the tether spans the growth plate. The first anchor, the second anchor, and the tether may cooperate to control new bone growth of the growth plate to correct a deformity of the patient's skeletal system. The method may include forming one or more incisions in the patient to implant the first and second anchors through the one or more incisions. The method may include closing the one or more incisions and slackening the growth-plate-spanning tether after closing the one or more incisions. The method may further include rotating one or more internal magnets of the first anchor by rotating one or more external magnets of an external adjustment device, thereby post-operatively and non-invasively actuating the actuator.

FIGS. 1-5 show an implant system 100 (FIG. 1) and features thereof, according to a first embodiment. In this embodiment, implant system 100 includes a tether 102 having a first end 102A opposite a second end 102B, a fixed bone anchor 104 configured to couple to the first end 102A, and an adjustable bone anchor 106 configured to couple to the second end 102B. Fixed bone anchor 104 includes a plate 108 coupled to a proximal end 110A of an externally threaded screw 110. Plate 108 includes an aperture (not shown) configured to receive and threadably engage the externally threaded screw 110 therein; in alternative embodiments, plate 108 and externally threaded screw 110 are integrally formed such that screw 110 extends from a bottom surface of plate 108. Plate 108 further includes an attachment feature 112 configured to couple to first end 102A of the tether 102. Attachment feature 112 may be in the form of, e.g., a hole or slot dimensioned to receive the tether 102 therethrough. The first end 102A of tether 102 may pass through, or be fixed to, attachment feature 112. Tether 102 extends between first end 102A (e.g., coupled to attachment feature 112 of fixed bone anchor 104) and second end 102B (e.g., coupled to adjustable bone anchor 106). Adjustable bone anchor 106 includes a housing 114 extending between a distal end 116B and a proximal end 116A. Adjustable bone anchor 106 includes a screw cap 121 coupled to proximal end 116A and configured to receive a portion of tether 102 therein. Screw cap 121 includes at least one aperture 130A, 130B configured to laterally receive the tether 102 therethrough. Adjustable bone anchor 106 further includes a bone engagement surface 118 adjacent the distal end 116B and an externally threaded portion 120 configured for engaging a bone (threads not shown).

Figure 3:
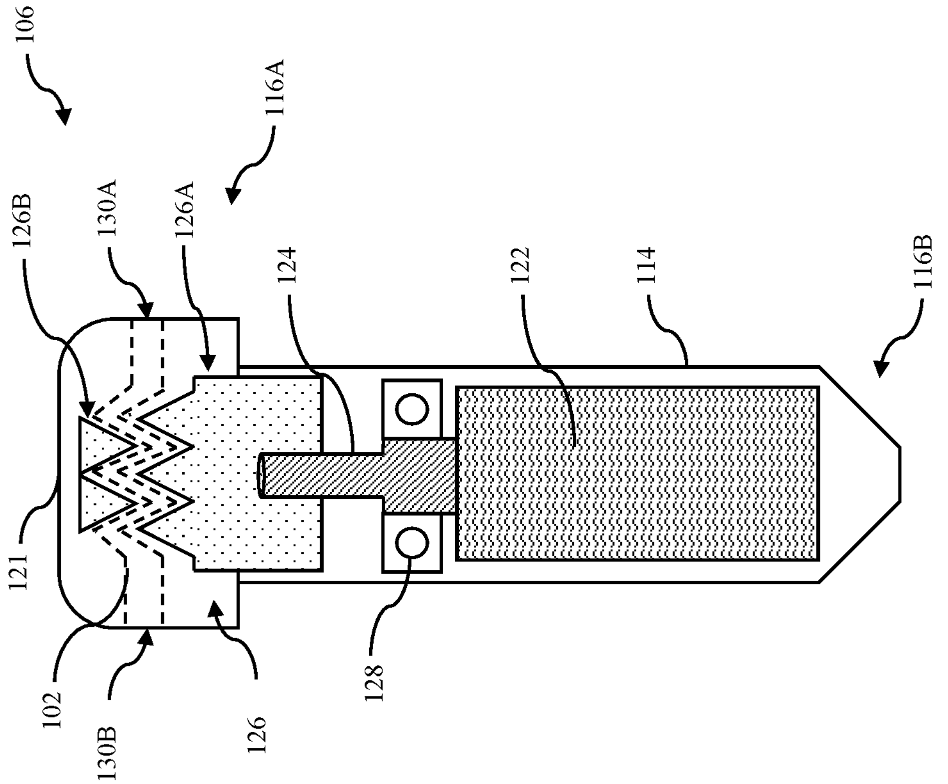
FIG. 3 illustrates a cross sectional view of an adjustable bone anchor of the implant system according to the first embodiment.
Figure 2:
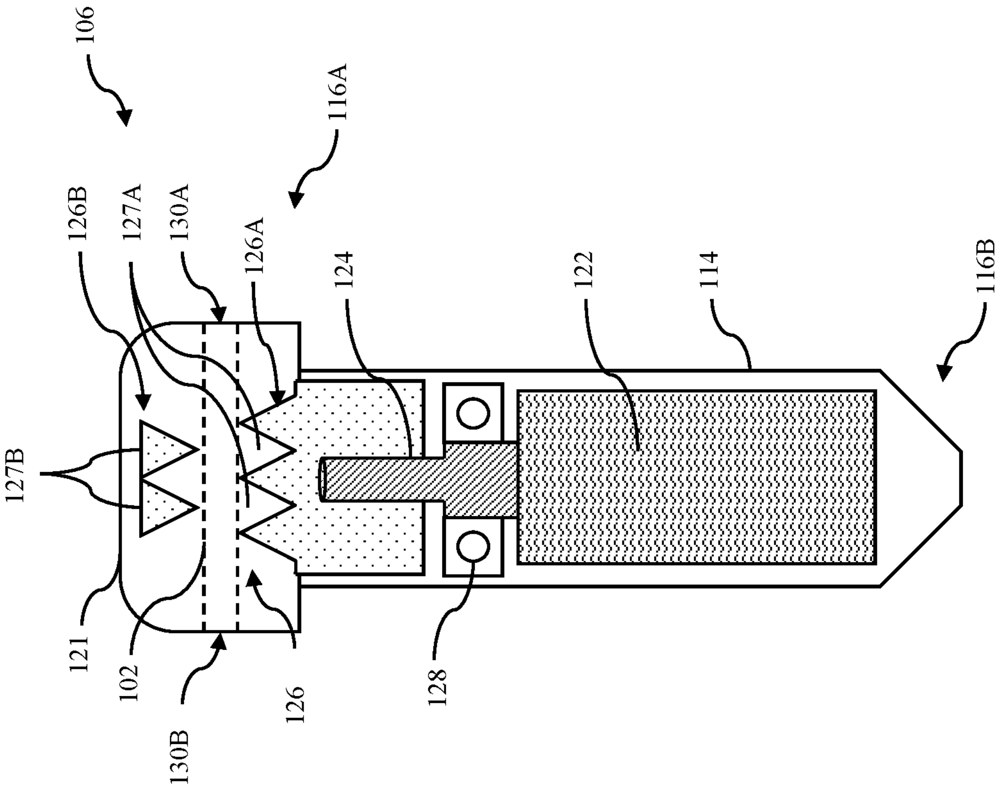
FIG. 2 illustrates a cross sectional view of an adjustable bone anchor of the implant system according to the first embodiment.

FIGS. 2 and 3 show cross-sectional views of adjustable bone anchor 106 according to the first embodiment. In this embodiment, adjustable bone anchor 106 includes a driver 122 disposed within housing 114. Driver 122 may be configured to drive rotational motion. Driver 122 may include a rotatable permanent magnet configured to be rotated by an externally applied magnetic field. An external adjustment device including an external magnet 414, 416 (see FIG. 18) may be configured to actuate rotation of the driver 122 in either of a first direction or a second direction about a rotational axis of the driver 122. Alternatively, driver 122 may include a motorconfigured to rotate in response to an electrical signal (e.g., as provided by an external device and optionally stored within the anchor 106). The motor may be electrically coupled to a power source such as, e.g., a battery or charging capacitor, to drive rotation of the motor output shaft. The power source may be configured for transcutaneous charging using an external power source.

As further shown by FIGS. 2 and 3, an output shaft 124 may extend proximally from, and be rotatably coupled to, the driver 122. Output shaft 124 and driver 122 are linearly fixed within the housing 114 by one or more bearings 128. Output shaft 124 may include an external threading configured to rotatably engage a clamping mechanism 126. Due to the threaded engagement between output shaft 124 and clamping mechanism 126, clamping mechanism 126 may be configured to translate linearly along the external threading of output shaft 124 in response to rotation of driver 122. The external magnet 414, 416 (FIG. 18) is configured to rotate in a first direction corresponding to translation of at least a portion of the clamping mechanism 126 in the proximal direction, resulting in locking of the clamping mechanism 126, and to rotate in a second direction corresponding to translation of at least a portion of the clamping mechanism 126 in the distal direction, resulting in unlocking the clamping mechanism 126, as described further herein.

Clamping mechanism 126 is configured to engage or disengage the tether 102 to increase or decrease grip on the tether 102, respectively. Clamping mechanism 126 includes a lower portion 126A and an upper portion 126B configured to secure the adjustable bone anchor 106 to the tether 102, which may be positioned between the lower and upper portions 126A, 126B of clamping mechanism 126. At least a portion of the tether 102 (shown in dashed lines in FIGS. 1-3) extends laterally through the adjustable bone anchor 106 between the lower and upper portions 126A, 126B of clamping mechanism 126, substantially perpendicularly relative to the rotational axis of the driver 122. As shown in FIGS. 2 and 3, screw cap 121 includes a pair of apertures 130A, 130B to laterally receive the tether 102 therethrough, and clamping mechanism 126 is positioned laterally between the pair of apertures 130A, 130B. Tether 102 extends laterally through each aperture 130A, 130B and axially between the lower and upper portions 126A, 126B of clamping mechanism 126. As shown in FIG. 2, in the unlocked position of adjustable bone anchor 106, tether 102 is free to move laterally within and in and out of screw cap 121. In this position, the movement of tether 102 is not restricted by clamping mechanism 126. When engaged with the tether 102, the clamping mechanism 126 can provide sufficient grip on the tether 102 to resist the tether 102 moving in or out of the screw cap 121 due to forces caused by growth of a growth plate.

Lower portion 126A is configured to rotatably engage, and translate linearly along a length of, the output shaft 124 in response to rotation of the driver 122 relative to the lower portion 126A. Lower portion 126A includes an internally threaded portion configured to threadably engage the external threading of output shaft 124 to translate proximally to engage, and distally to disengage, the upper portion 126B of clamping mechanism 126. Upper portion 126B is disposed within a recess of the screw cap and configured to couple to an inner surface of the screw cap 121. Upper portion 126B is therefore axially fixed with respect to screw cap 121. As a result, translation of lower portion 126A relative to output shaft 124 also results in translation of lower portion 126A relative to upper portion 126B. Relative to FIG. 2, the adjustable bone anchor 106 of FIG. 3 illustrates the position of lower portion 126A after translating in a proximal direction as described herein to engage the upper portion 126B of the clamping mechanism 126.

The upper portion 126B and the lower portion 126A can have any of a variety of different features configured to facilitate gripping a tether disposed therebetween, such as various geometries or surface features (e.g., knurling or other textures). In some examples, one or both of the upper portion 126B and the lower portion 126A include one or more features configured to engage with complimentary features of a tether (e.g., holes, tabs, or other structures). In the illustrated example, the upper portion 126B includes one or more features having a substantially conical or pyramidal three dimensional shape, or a triangular cross sectional shape, configured to engage a recess in lower portion 126A having a corresponding and complementary shape. In the embodiment shown in FIGS. 2-3, two such features 127B are shown in upper portion 126B, and two such recesses 127A are shown in lower portion 126A. As shown in FIG. 3, upon proximal translation of lower portion 126A toward upper portion 126B, the tether 102 becomes clamped between the corresponding features 127B and recesses 127A. This clamping secures the lateral position of tether

102 relative to adjustable bone anchor 106, and limits lateral movement of the tether 102 relative to the adjustable bone anchor 106.

In other embodiments discussed herein, the lower portion 126A and/or upper portion 126B have a different geometrical configuration to engage or disengage the tether 102 disposed therebetween.

Figure 5:
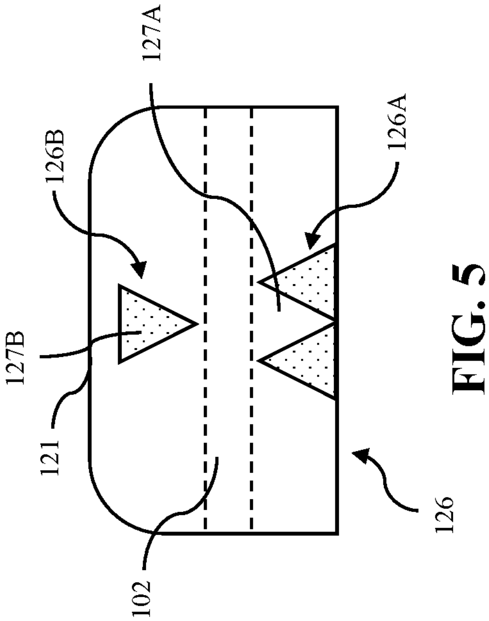
FIGS. 4 and 5 illustrate cross sectional views of various embodiments of a clamping mechanism of the adjustable bone anchor according to the first embodiment.
Figure 4:
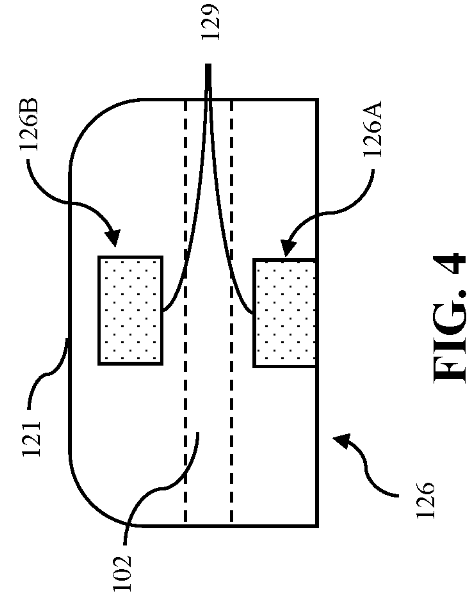

FIGS. 4-5 illustrate various embodiments of the clamping mechanism 126, each in their unlocked positions. In some embodiments, as shown in FIG. 4, the lower and upper portions 126A, 126B of the clamping mechanism 126 each include a feature having a flat surface 129 to engage or disengage the tether 102 in response to actuation of the driver 122. With reference to FIG. 5, in some embodiments, one of the lower and upper portions 126A, 126B of the clamping mechanism 126 includes a feature 127B having a substantially conical or pyramidal three dimensional shape, or a triangular cross sectional shape, and the other of the lower and upper portions 126A, 126B includes a recess configured to receive the triangular feature. This embodiment is similar to that of FIGS. 2-3 but may include fewer or greater of each of features 127B and recesses 127A. For example, as shown in FIG. 5, upper portion 126B includes one conical feature 127B configured to engage or disengage one complementary recess 127A in lower portion 126A. Other numbers of features 127B and recesses 127A are also possible such as, e.g., three or more features and corresponding recesses. In other embodiments, one of the lower and upper portions 126A, 126B of the clamping mechanism 126 includes a barbed surface, and the other of the lower and upper portions 126A, 126B includes a recess configured to receive the barbed surface therein. In other embodiments, at least one of the lower and upper portions 126A, 126B of the clamping mechanism 126 includes a barbed surface on at least one side thereof. In other embodiments, one of the lower and upper portions 126A, 126B of the clamping mechanism includes two features, each having a conical or pyramidal three dimensional shape, or a triangular cross sectional shape, and the other one of the lower and upper portions 126A, 126B includes two recesses configured to receive the corresponding features therein. In each example, the arrangement of features and recesses may be reversed, such that the features and recesses are each disposed on the opposite portion 126A, 126B of the clamping mechanism from what is pictured.

Figure 6:
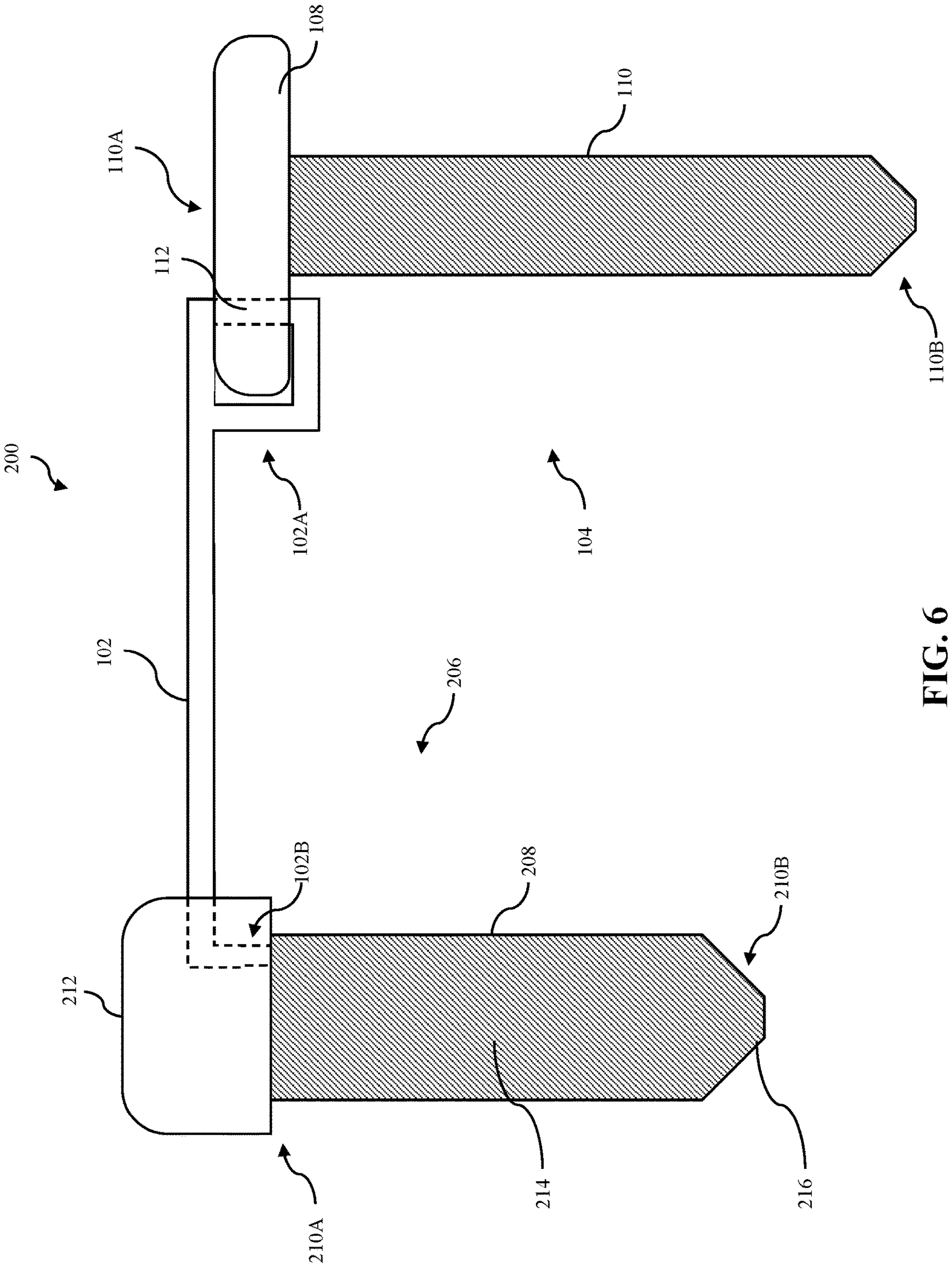
FIG. 6 illustrates a side view of an implant system according to a second embodiment.
Figure 7:
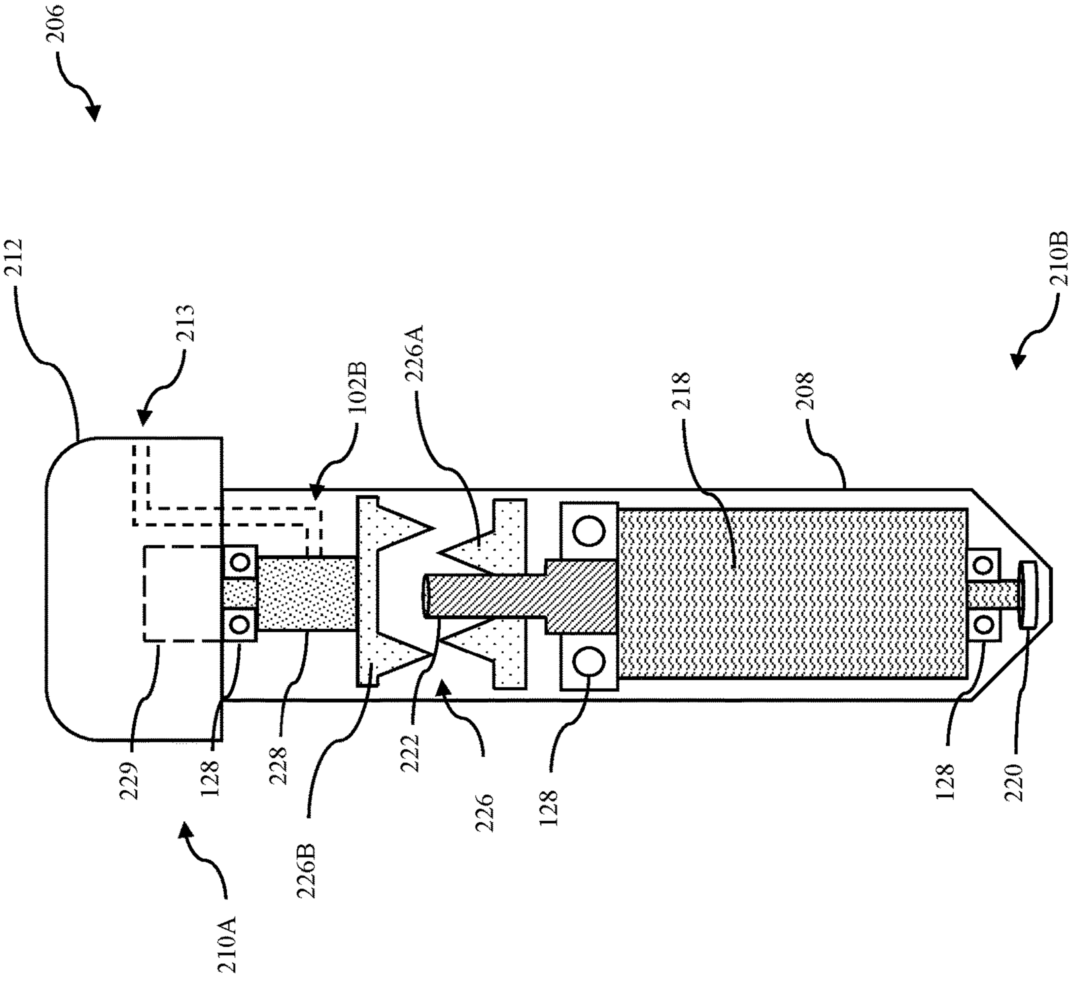
FIG. 7 illustrates a cross sectional view of an adjustable bone anchor of the implant system according to the second embodiment.
Figure 8:
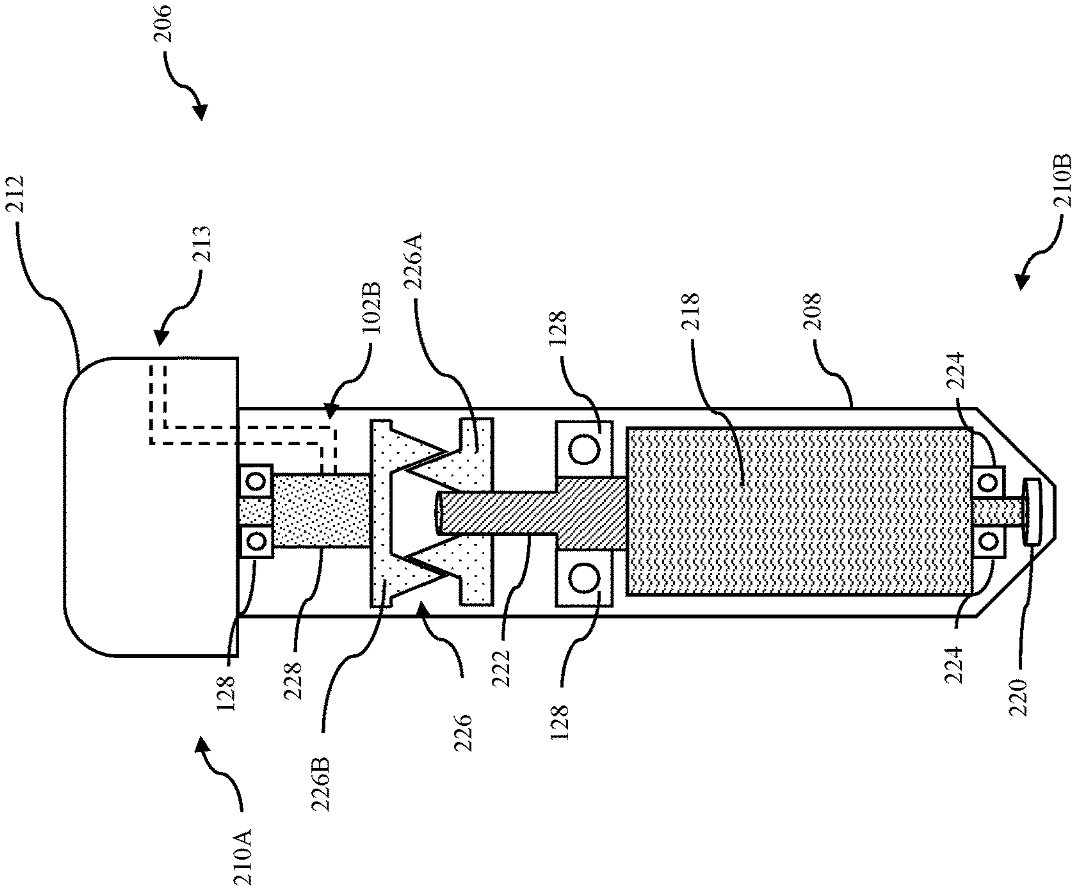
FIG. 8 illustrates a cross sectional view of an adjustable bone anchor of the implant system according to the second embodiment.

FIGS. 6-8 show an implant system 200 (FIG. 6) and features thereof, according to a second embodiment. In this embodiment, implant system 200 includes tether 102 having first end 102A opposite second end 102B, fixed bone anchor 104 configured to couple to the first end 102A, and an adjustable bone anchor 206 configured to couple to the second end 102B. Tether 102 and fixed bone anchor 104 include similar features to other embodiments discussed herein (e.g., system 100 of the first embodiment shown in FIGS. 1-5) and will not be reiterated for brevity. Adjustable bone anchor 206 includes a housing 208 extending between a distal end 210B and a proximal end 210A. Adjustable bone anchor 206 may include a screw cap 212 coupled to proximal end 210A and configured to receive a portion of tether 102 therein. Screw cap 212 may include at least one aperture, e.g., a guide slot 213 (FIG. 7) configured to laterally receive tether 102 therethrough. Adjustable bone anchor 206 may further include a bone engagement surface 216 (FIG. 6) adjacent to distal end 210B and an externally threaded portion 214 configured for engaging a bone. The threads of threaded portion 214 are not shown in FIGS. 6-8, but may be analogous to, e.g., the threads of screw 510 in FIG. 12.

Adjustable bone anchor 206 may be configured to wind or unwind a portion of tether 102 disposed therein to increase or decrease tension on tether 102, respectively. In addition or instead, the adjustable bone anchor 206 can be configured to lock or unlock the ability of a spool to rotate, thereby disallowing or allowing a portion of tether 102 to wind or unwind.

FIGS. 7 and 8 show a cross-sectional view of the adjustable bone anchor 206 according to FIG. 6. In this embodiment, adjustable bone anchor 206 includes a driver 218 disposed within housing 208. Driver 218 may be configured to drive rotational motion. Driver 218 may include a rotatable permanent magnet configured to be rotated by an externally applied magnetic field. An external adjustment device including an external magnet 414, 416 (see FIG. 18) may be configured to actuate rotation of the driver 218 in either of a first direction or a second direction about a rotational axis of driver 218. The first direction may be one of, and the second direction may be the other of, clockwise and counterclockwise. An output shaft 222 may extend proximally from, and be rotatably coupled to, the driver 218. Output shaft 222 and driver 218 may be axially fixed within the housing 208 by one or more mechanical hardware components such as, e.g., one or more bearings 128. Output shaft 222 may include an external threading, e.g., male threading, configured to rotatably engage a locking mechanism 226 having internal threading, e.g., female threading. Due to the threaded engagement between output shaft 222 and locking mechanism 226, locking mechanism 226 may be configured to translate axially along the external threading of output shaft 222 in response to rotation of driver 218. Rotation of driver 218 in a first direction may correspond to translation of at least a portion of the locking mechanism 226 in the proximal direction, resulting in achievement of a locked position of the locking mechanism 226 (FIG. 8), while rotation of driver 218 in a second direction, which may correspond to translation of at least a portion of the locking mechanism 226 in the distal direction, may result in achievement of an unlocked position of the locking mechanism 226 (FIG. 7). Locking mechanism 226 may be configured to increase or decrease tension in the tether 102 when in the locked or unlocked position, respectively. Locking mechanism 226 may be configured to permit or resist rotation of a spool 228 to permit modification of tension in the tether 102 that would otherwise be resisted by the engagement of the locking mechanism 226.

Locking mechanism 226 may include a distal portion 226A having proximal facing teeth positioned opposite a proximal portion 226B having distally facing teeth. The proximal facing teeth of distal portion 226A may be configured to engage or disengage the distally facing teeth of proximal portion 226B, which may be axially fixed, to lock or unlock the locking mechanism 226, respectively. Distal portion 226A may include an internal threading configured to rotatably engage an external threading of output shaft 222. Due to the threaded engagement between output shaft 222 and distal portion 226A of locking mechanism 226, distal portion 226A may be configured to translate axially along the external threading of output shaft 222 in response to actuation of driver 218. In embodiments in which driver 218 is a magnet, the external magnets 414, 416 of the external adjustment device 400 (FIG. 18) may be configured to actuate rotation of driver 218 to axially translate distal portion 226A in either of a first, e.g., proximal direction to engage the proximal portion 226B (i.e., locked position of locking mechanism 226), or a second, e.g., distal direction to disengage the proximal portion 226B (i.e., unlocked position of locking mechanism 226). Proximal portion 226B of locking mechanism 226 may further include a spool 228 extending proximally therefrom. The spool 228 may be fixed radially and/or axially within housing 208 using one or more hardware components such as, e.g., bearings 128. Second end 102B of tether 102 may couple to spool 228 and a portion of tether 102 may wind around spool 228 to increase tension on tether 102. When locking mechanism 226 is in the unlocked position, spool 228 may be configured to rotate freely about an axis of rotation and permit decreased tension in tether 102. When locking mechanism 226 is in the locked position, spool 228 may be rotationally fixed about the axis of rotation so as to maintain length and therefore tension in tether 102. In other examples, the anchor 206 lacks the locking mechanism 226, and instead the actuation of the driver 218 causes rotation of the spool 228, which directly increases or decreases tension in the tether 102. In some examples, the anchor 206 include one or more manual actuation elements that permit a user to intraoperatively lock or unlock the locking mechanism 226 or wind or unwind the spool 228 manually.

Adjustable bone anchor 206 may further include screw cap 212 having one or more guide slots 213 configured to receive tether 102 therethrough. Although shown as having one guide slot 213, screw cap 212 may include two or more guide slots 213 in alternative embodiments. The one or more guide slots 213 may be configured to engage a driver (not shown) during implantation of adjustable bone anchor 206. The driver may be configured to couple to adjustable bone anchor 206 such that rotation of the driver rotates the adjustable bone anchor 206. The driver may include a mechanism at a distal end thereof (e.g., one or more prongs) dimensioned to be received through the one or more guide slots 213 to extend into screw cap 212 and couple the driver to adjustable bone anchor 206. The driver may include a mechanism to engage or disengage the adjustable bone anchor 206 by extending or retracting the mechanism, respectively, through the one or more guide slots 213. In some embodiments, screw cap 212 may further include a recess 229 configured to receive a proximal portion of spool 228 therein.

Figure 16:
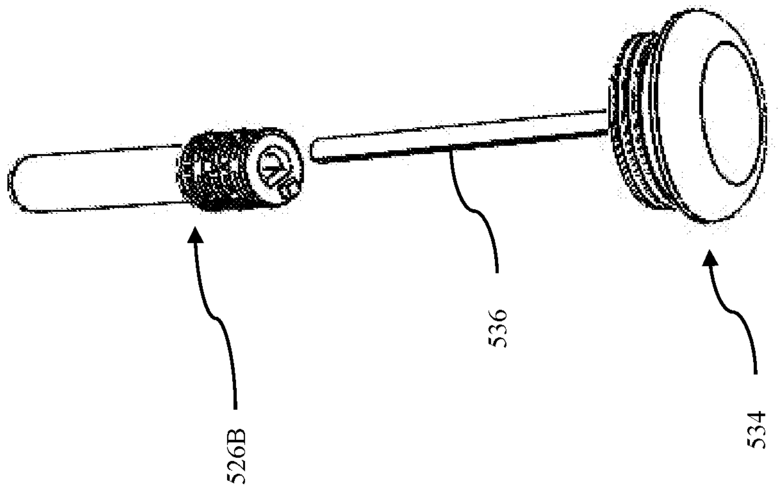
FIGS. 15-16 illustrate exploded view of aspects of the adjustable bone anchor according to the fourth embodiment.

Adjustable bone anchor 206 may further include a magnetic brake 220 disposed within housing 208 and proximate to the distal end 210B. Magnetic brake 220 may keep the adjustable bone anchor 206 from being accidentally adjusted by movements of a patient when implanted. An enlarged view of magnetic brake 220 is shown in FIG. 16. Magnetic brake 220 is positioned proximate and axially spaced from a distal end of driver 218. Magnetic brake 220 may include a magnetically permeable material, such as 400 series stainless steel. As shown in FIG. 16, magnetic brake 220 may include a portion that is generally cylindrical in shape and includes at least two tabs 215 separated by gaps. When the adjustable bone anchor 206 is not being adjusted (e.g., using an external adjustment device), the magnetic poles of the radially-poled cylindrical magnet are magnetically attracted to tabs 215. However, when driver 218 is forced to rotate due to the effect of a sufficiently large rotating magnetic field, driver 218 overcomes the smaller attractions of tabs 215. Magnetic brake 220 may also include a flanged extension and/or flanged extension fingers 217 for engaging a housing. Additional details of the magnetic brake 220 can be found in U.S. Pat. Pub. 2019/0015138, filed Jul. 26, 2018, which is incorporated herein by reference as if set forth in its entirety.

Referring back to FIGS. 6-8, in some embodiments, adjustable bone anchor 206 may include a second driver (not shown) disposed within a cavity of spool 228. The second driver may be configured to drive rotational motion in spool 228. The second driver may be configured to rotate spool 228 in either of a first direction corresponding to winding tether 102 around spool 228, and a second direction corresponding to unwinding tether 102 from spool 228. The second driver may include, for example, a rotatable permanent magnet or a motor. In embodiments where the second driver includes a rotatable permanent magnet, the second driver may be configured to rotate in either of the first or second direction in response to an external magnetic field applied from an external adjustment device (see FIG. 18). In embodiments where the second driver includes a motor, the second driver may be configured to rotate spool 228 in either of the first or second direction in response to an external electrical signal (not shown). The motor may be electrically coupled to a power source (e.g., a battery, charging capacitor, etc.) configured to drive rotation of the motor in response to the external electrical signal. The power source may be configured for transcutaneous wireless charging from an external power source (not shown).

Figure 9:
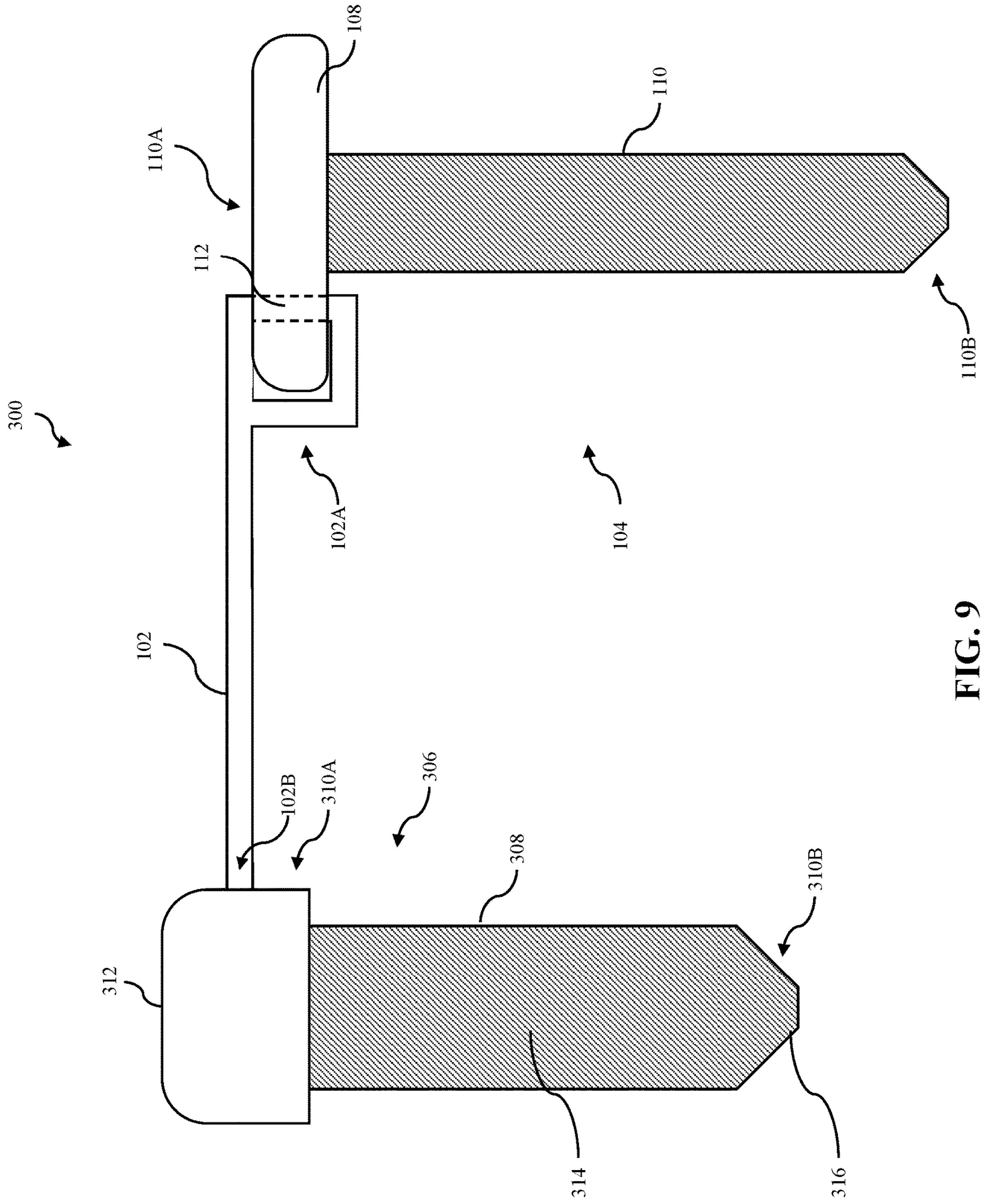
FIG. 9 illustrates a side view of an implant system according to a third embodiment.
Figure 10:
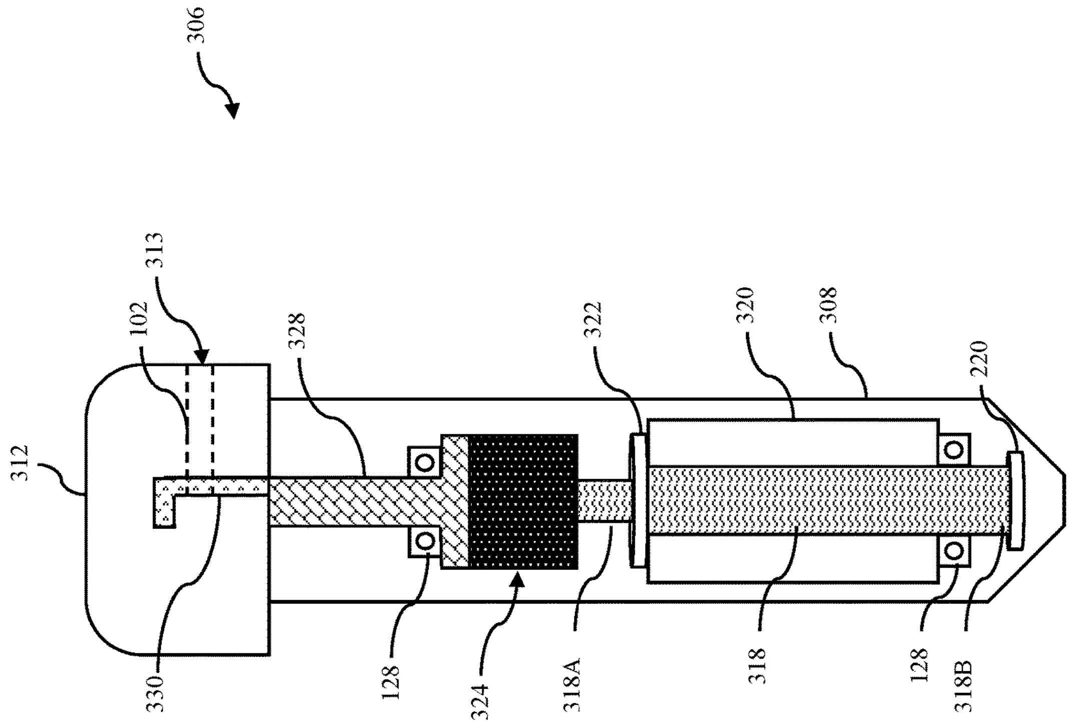
FIG. 10 illustrates a cross sectional view of an adjustable bone anchor of the implant system according to the third embodiment.
Figure 11:
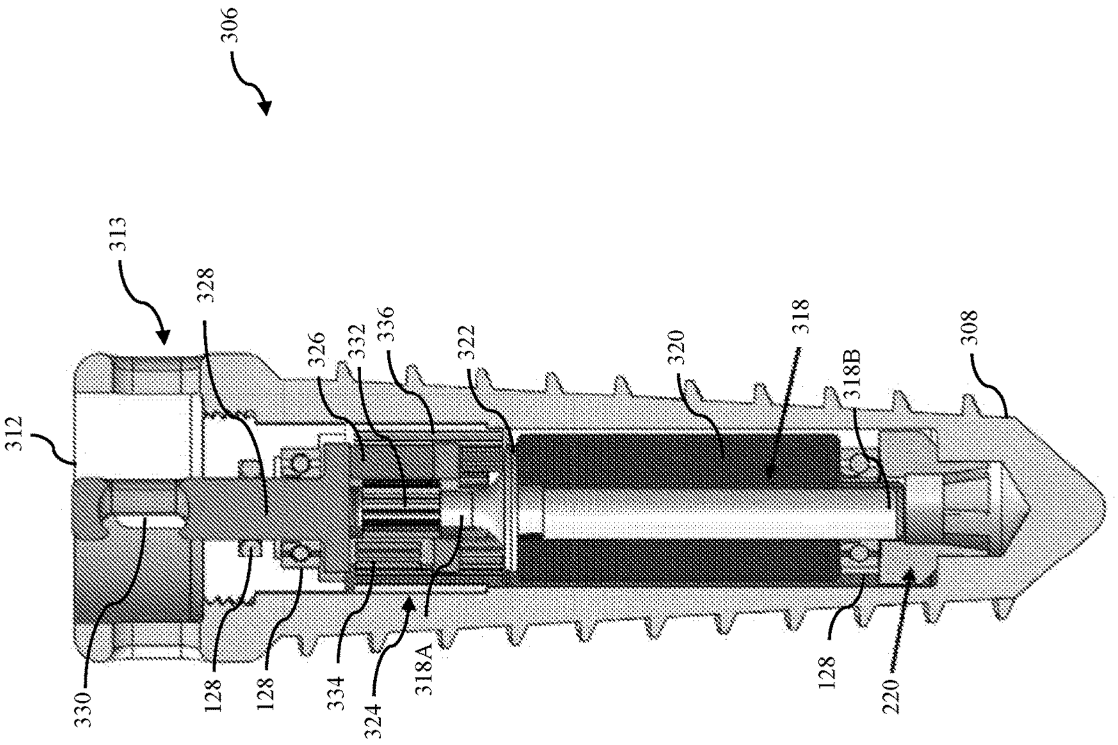
FIG. 11 illustrates a cross sectional view of the adjustable bone anchor of the implant system according to the third embodiment.

FIGS. 9-11 show an implant system 300 (FIG. 9) and features thereof, according to a third embodiment. In this embodiment, implant system 300 includes tether 102 having first end 102A opposite second end 102B, a fixed bone anchor 104 configured to couple to the first end 102A, and an adjustable bone anchor 306 configured to couple to the second end 102B. Tether 102 and fixed bone anchor 104 include similar features to other embodiments discussed herein (e.g., system 100 of FIGS. 1-5, and system 200 of FIGS. 6-8) and will not be reiterated for brevity.

Adjustable bone anchor 306 includes a housing 308 extending between a distal end 310B and a proximal end 310A. Adjustable bone anchor 306 may include an end cap 312 coupled to proximal end 310A and configured to seal housing 308 and components disposed therein. End cap 312 may include at least one aperture (e.g., a guide slot 313, shown in FIG. 10) configured to receive tether 102 therethrough. Adjustable bone anchor 306 may further include a bone engagement surface 316 adjacent distal end 310B and an externally threaded portion 314 configured for engaging a bone. Adjustable bone anchor 306 may be configured to wind or unwind a portion of tether 102 disposed therein to increase or decrease tension on tether 102, respectively.

FIG. 10 shows a cross sectional view of adjustable bone anchor 306 according to the embodiment of FIG. 9. In this embodiment, adjustable bone anchor 306 includes a driver 318 disposed within housing 308. Driver 318 may be configured to drive rotational motion. Driver 318 may include a rotatable permanent magnet configured to be rotated by an externally applied magnetic field. An external adjustment device including an external magnet 414, 416 (FIG. 18) may be configured to actuate rotation of driver 318 in either of a first direction or a second direction about a rotational axis of driver 318. Driver 318 may include a rotatable permanent magnet having a cross sectional shape including at least one line and at least one arc, e.g., semi-circular, crescent shaped, or D-shaped, and configured to engage a correspondingly and matingly shaped, e.g., D-hole drive 320.

Adjustable bone anchor 306 may further include a gear system 324 coupled to a proximal end 318A of driver 318. Gear system 324 may include one or more stages of gears such as, e.g., planetary gears. In the embodiment shown in FIG. 10, gear system 324 includes one stage of planetary gears, but it should be understood that any number of stages may be implemented in various embodiments within the scope of the present disclosure. Each stage of the one or more stages of gears in gear system 324 may provide a torque multiplier such as, e.g., a 4:1 torque multiplier. An output member 328 may extend proximally from, and be rotatably coupled to, gear system 324 such that rotation of driver 318 rotates the output member 328 in either of a first direction or a second direction about a rotational axis of driver 318. In the embodiment shown in FIG. 11, the gear system 324 includes a sun gear 332 rotatably coupled to the proximal end 318A of driver 318. Driver 318 rotates the sun gear 332 in either of a first direction or a second direction about a rotational axis of driver 318. Sun gear 332 is configured to rotatably engage a set of planetary gears 334 disposed within a ring gear 336 such that rotating the driver 318 rotates the set of planetary gears 334 about a rotational axis of the sun gear 332. The set of planetary gears 334 may be configured to rotate a carrier 326 disposed therein. Output member 328 may extend proximally from, and be rotatably coupled to, the carrier 326. Rotation of the driver 318 therefore rotates the sun gear 332, which in turn rotates the set of planetary gears 334, which in turn rotates the carrier 326, and which in turn rotates the output member 328.

Output member 328 may include a spool 330 extending proximally therefrom and configured to receive the tether 102 thereon. The spool 330 may include a hook shape at a proximal end thereof to prevent the tether 102 from sliding off the spool 330 in a proximal direction. Although spool 330 is shown as having a hook shape in FIGS. 10 and 11, the spool 330 may include a different shape configured to retain the tether 102 thereon. In some embodiments, the spool 330 may include one or more slots at a proximal end thereof configured to laterally receive tether 102 therethrough. Second end 102B of tether 102 may fixedly couple to output member 328, and a portion of the tether 102 winds around spool 330. An external magnet 414, 416 of the external adjustment device 400 (FIG. 18) may be configured to actuate rotation of driver 318 to rotate spool 330 in either of a first direction corresponding to increased tension in tether 102, and a second direction corresponding to decreased tension in tether 102. The first direction may be one of, and the second direction may be the other of, clockwise and counterclockwise. Rotating spool 330 in the first direction winds tether 102 around spool 330, thereby removing slack in tether 102 to increase tension. Rotating spool 330 in the second direction may unwind tether 102 from around spool 330, thereby increasing slack in tether 102 to decrease tension. Depending on the direction in which tether 102 is wound around spool 330, the first direction may be clockwise or counterclockwise, with the second direction being opposite the first direction.

Adjustable bone anchor 306 may further include end cap 312 configured to seal the proximal end 310A of housing 308, and thus seal components disposed therein (e.g., driver 318, output member 328, etc.). A biocompatible composition such as, e.g., epoxy, may seal end cap 312 to housing 308. A guide slot 313 in communication with spool 330 may be disposed proximally relative to end cap 312. Guide slot 313 may be configured to laterally receive tether 102 therethrough and enable winding of tether 102 around the spool 330. Guide slot 313 may be configured to engage a driver tool (not shown) to facilitate implantation of adjustable bone anchor 306 into a bone. Although one guide slot 313 is illustrated in the adjustable bone anchor 306 of FIG. 10, one or more guide slots 313 in end cap 312 are within the scope of the present disclosure. In some embodiments, for example, end cap 312 includes four guide slots 313 spaced, e.g., equidistant from one another, about a perimeter, e.g. circumference, of end cap 312. The one or more guide slots 313 may be useful to receive tether 102 therethrough and/or engage a driver tool during implantation of adjustable bone anchor 306.

Adjustable bone anchor 306 may further include magnet brake 220 coupled to distal end 318B of driver 318. Magnetic brake 220 is similar to other embodiments discussed herein (see FIG. 16) and will not be elaborated on for brevity.

FIGS. 12-16 illustrate an implant system 500 (FIGS. 12-13) and features thereof, according to a fourth embodiment. In this embodiment, implant system 500 includes a tether 502 having a first end 502A opposite a second end 502B, a fixed bone anchor 504 configured to couple to the first end 502A of the tether 502, and an adjustable bone anchor 506 configured to couple to the second end 502B of the tether 502. Fixed bone anchor 504 includes a plate 508 coupled to a proximal end 510A of an externally threaded screw 510. Plate 508 may include a hole 515 (see FIG. 13) configured to receive and threadably engage externally threaded screw 510 therein; in alternative embodiments, plate 508 and externally threaded screw 510 are integrally formed such that screw 510 extends from a bottom surface of plate 508. Plate 508 may include an aperture 518 configured to receive and couple to first end 502A of the tether 502. Plate 508 may further include an attachment feature 520 configured to couple to tether 502 at a point 502D between the first and second ends 502A, 502B of tether 502. Attachment feature 520 may be in the form of, e.g., a hole dimensioned to receive the tether 502 therethrough. Adjustable bone anchor 506 includes a housing 512 extending between a distal end 512B and a proximal end 512A. A plate 514 is coupled to the proximal end 512A and a bone engagement surface 516 is proximate to the distal end 512B. Plate 514 includes an aperture 522 configured to receive at least a portion of a connector 526 therein. For example, proximal portion 526A of connector 526 may be configured to couple to second end 502B of tether 502, as shown in detail in FIG. 14. Proximal portion 526A of connector 526 may be bulbous, ovoid, spherical, or substantially spherical in shape, however other shapes and configurations of connector 526 are within the scope of the present disclosure. Proximal portion 526A may further include an annular groove or indentation 527 configured to receive a portion of the second end 502B therein. For example, the second end 502B may include a hole 528 through which the proximal portion 526A may be inserted until the second end 502B rests within the groove 527. Groove 527 thus resists or reduces likelihood of translation of second end 502B relative to proximal portion 526A, particularly in a proximal direction, and therefore resists or reduces likelihood of disengagement of second end 502B of tether 502 from proximal portion 526A. Plate 514 may further include an attachment feature 524 configured to couple to the tether 502 at a point 502C between the first and second ends 502A, 502B of tether 502. Attachment feature 524 may be, e.g., a hole through which tether 502 passes.

Figure 12:
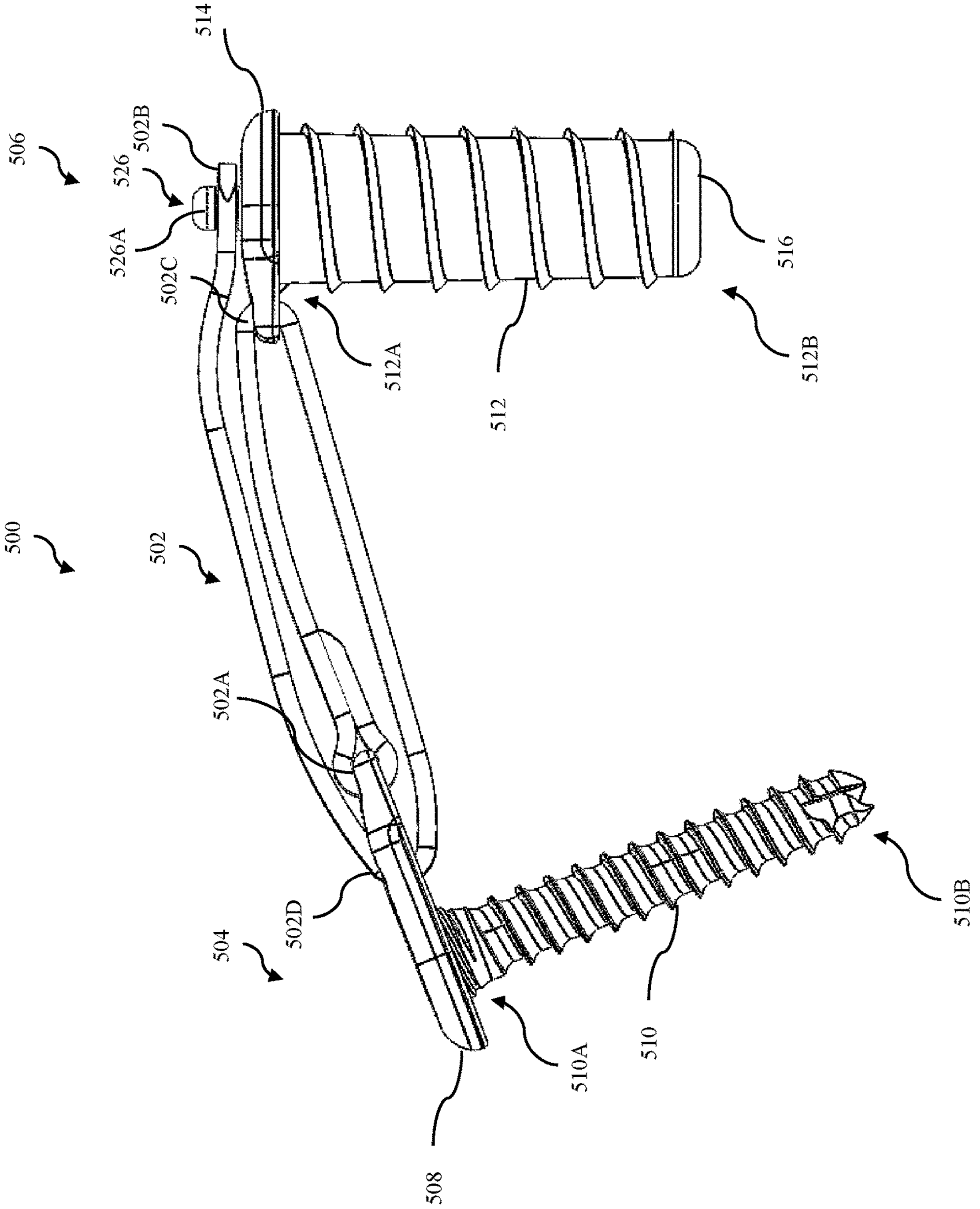
FIG. 12 illustrates a side view of an implant system according to a fourth embodiment.
Figure 13:
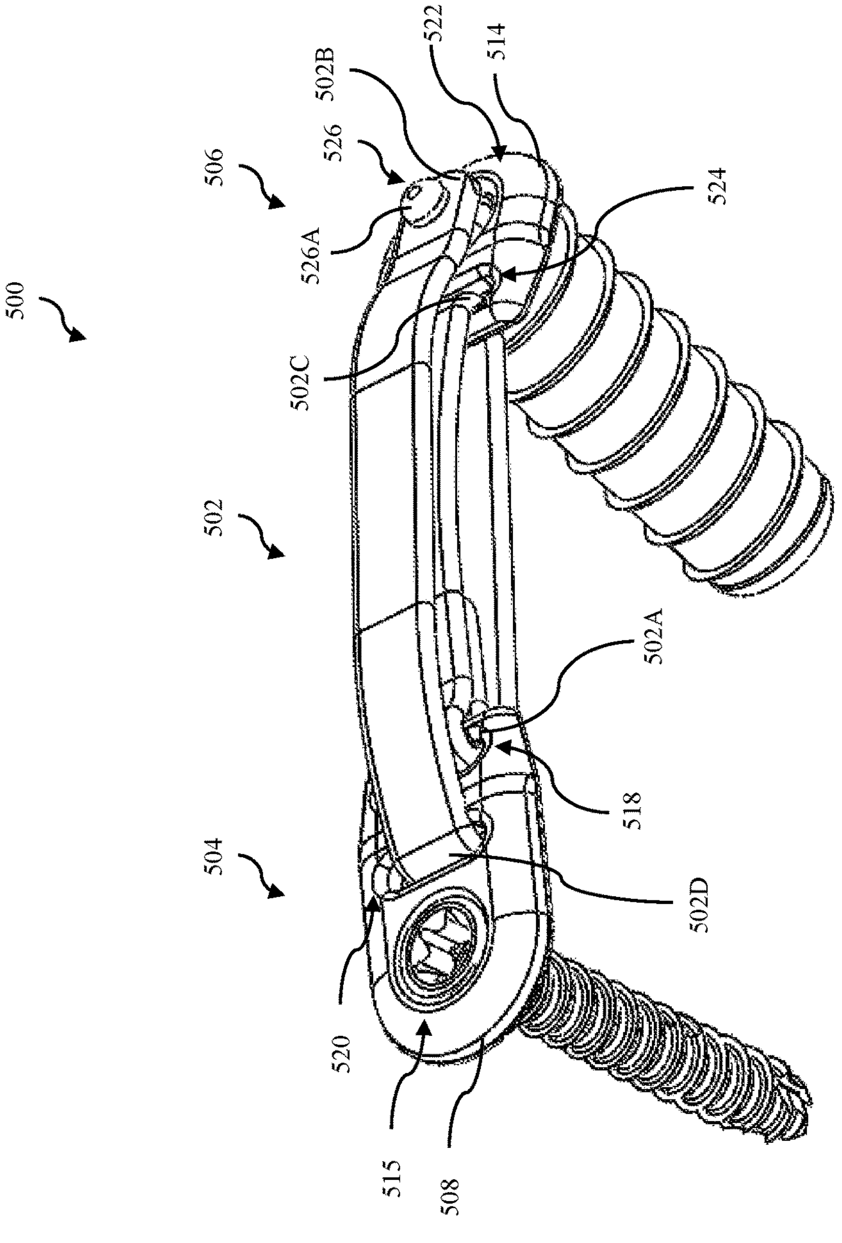
FIG. 13 illustrates a perspective view of the implant system according to the fourth embodiment.

As shown in FIGS. 12-13, first end 502A of tether 502 is coupled to aperture 518 in plate 508 of the fixed bone anchor, and second end 502B is coupled to proximal portion 526A of connector 526. Intermediate points 502C, 50D are illustrated as two points along tether 502 between the first end 502A and the second end 502B, which engage, e.g., extend through the respective attachment features 520, 524. The positions of intermediate points 502C and 502D are identified on FIGS. 12-13 as specific positions on tether 502. However, the locations of points 502C and 502D along tether 502 may shift as tether 502 is adjusted. The position of points 502C and 502D may be defined primarily by their engagement with their respective attachment features 520, 524, which may not be static. In embodiments including attachment features 520 and 524, the tether 502 extends from the first end 502A to and through attachment feature 524 of plate 514 at point 502C. Tether 502 then extends from point 502C to and through attachment feature 520 of plate 508 at point 502D. Tether 502 then extends from point 502D to the second end 502B, which is coupled to the proximal portion 526A of connector 526. Connector 526 may be configured to translate axially in a distal or proximal direction relative to adjustable bone anchor 506, thereby increasing or decreasing tension on tether 502, respectively. In certain other embodiments, attachment features 520, 524 and points 502C and 502D may be omitted, such that the tether simply extends from first end 502A to second end 502B, coupling aperture 518 in plate 508 to connector 526 at plate 514. However, embodiments such as the one depicted in FIGS. 12-13, which includes attachment features 520, 524 and points 502C and 502D, provide a mechanical advantage over embodiments lacking these features. This mechanical advantage may reduce the force required to cause axial translation of connector 526 as described herein. This may in turn facilitate the use of a smaller magnet.

Figure 14:
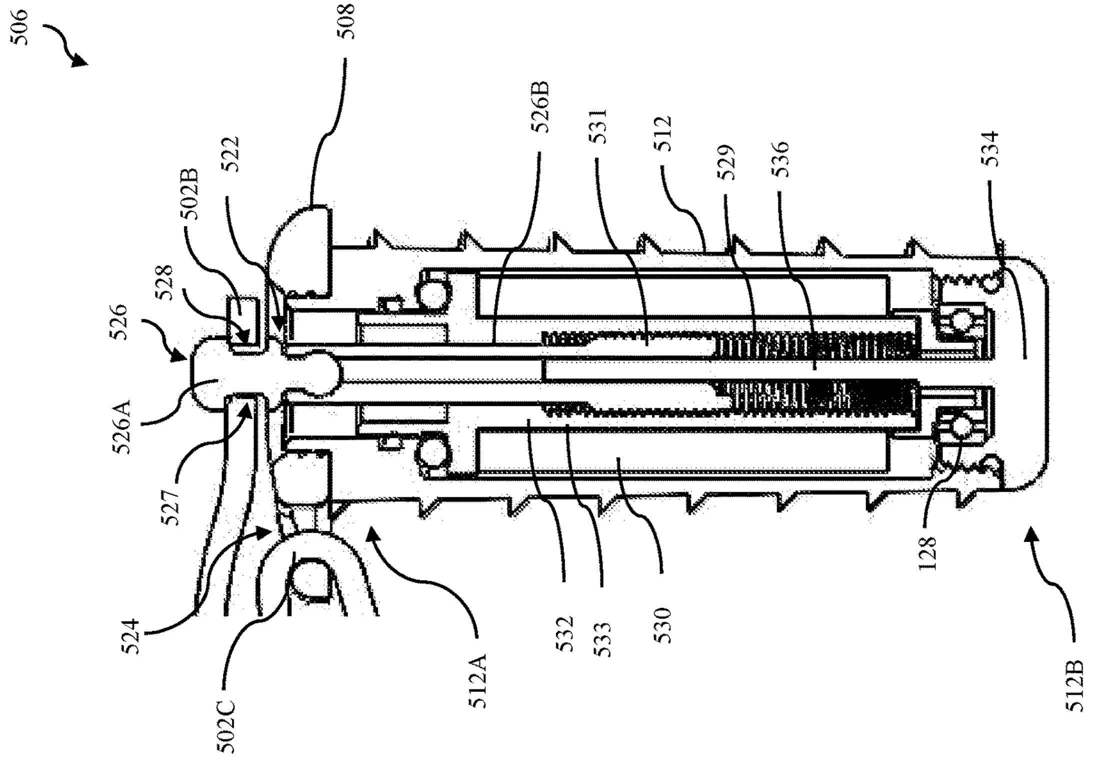
FIG. 14 illustrates a cross sectional view of an adjustable bone anchor of the implant system according to the fourth embodiment.

FIG. 14 shows a cross-sectional view of adjustable bone anchor 506 of implant system 500 as shown in FIGS. 12-13. In the present embodiment, adjustable bone anchor 506 includes a driver 530 disposed within the housing 512. Driver 530 may be configured to drive rotational motion. Driver 530 may include a rotatable permanent magnet configured to be rotated by an externally applied magnetic field. An external adjustment device including an external magnet 414, 416 (FIG. 18) may be configured to actuate rotation of driver 530 in either of a first direction or a second direction about a rotational axis of driver 530 to increase or decrease tension on tether 502, respectively. The external magnet 414, 416 (FIG. 18) may be configured to actuate rotation of driver 530 in either of a first direction selected from clockwise and counterclockwise, corresponding to axial translation of connector 526 in a distal direction, or a second direction opposite the first direction, corresponding to axial translation of connector 526 in a proximal direction. Driver 530 may include a rotatable permanent magnet having an opening 533 extending axially therethrough. The opening 533 may have a cross sectional shape including at least one line and at least one arc, e.g., semi-circular, crescent shaped, or D-shaped, and be configured to receive a matingly shaped component therein such as, e.g., an output member 532.

Figure 15:
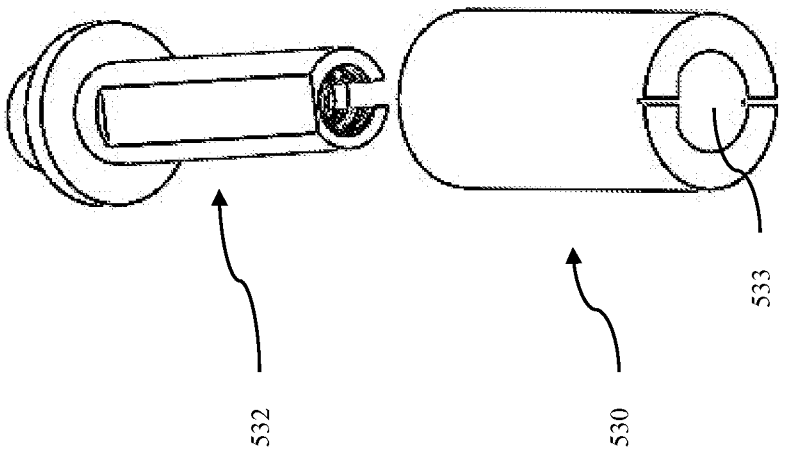
Figure 17:
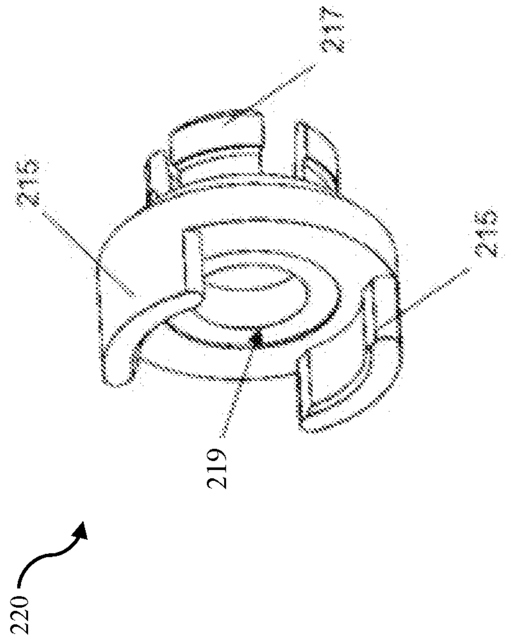
FIG. 17 illustrates a perspective view of a magnetic brake according to embodiments of the invention.

FIG. 15 shows an exploded perspective view of the driver 530 and output member 532 according to the embodiment of FIGS. 12-14. In the present embodiment, the driver 530 includes a cylindrical or substantially cylindrical rotatable permanent magnet having an opening 533 therein configured to receive the output member 532. The geometry of the cross sectional shape of the output member 532 may be configured to correspond to and complement the geometry of the cross sectional shape of the opening 533 in driver 530. The output member 532 may include a first portion configured to be received within the driver 530 and a second portion extending proximally therefrom. The output member 532 may be rotatably coupled or affixed to the driver 530 such that actuating rotation of the driver 530 simultaneously rotates the output member 532 in the same direction about a rotational axis of the driver 530.

Referring back to FIG. 14, the output member 532 may include an internal threading 529 configured to rotatably engage a distal portion 526B of connector 526 disposed thereon. The distal portion 526B of connector 526 may include external threads 531 configured to matingly engage with internal threads 529. Due to the threaded engagement between output member 532 and connector 526, the connector 526 may be configured to translate axially along the internal threading 529 of output member 532 in response to rotation of the driver 530. Rotation of driver 530 in a first direction may correspond to translation of the connector 526 in the proximal direction, and may result in decreased tension on the tether 102, while rotation of driver 530 in a second direction, which may correspond to translation of the connector 526 in the distal direction, may result in increased tension on the tether 102. Translation of the distal portion 526B of connector 526 in the proximal direction may similarly cause translation of the proximal portion 526A of connector 526 in the proximal direction such that the proximal portion 526A moves away from the groove 527, thereby releasing tension on the second end 102B of tether 102 resting within the groove 527. Translation of the distal portion 526B of connector 526 in the distal direction may similarly cause translation of the proximal portion 526A of connector 526 in the distal direction such that the proximal portion 526A moves toward the groove 527, thereby increasing tension on the second end 102B of tether 102 resting within the groove 527.

The distal portion 526B of connector 526 may include a cross sectional shape including at least one line and at least one arc, e.g., semi-circular, crescent shaped, or D-shaped, and be configured to receive a matingly shaped component therein such as, e.g., an end cap guide 536. The end cap guide 536 may include an elongate member configured to guide axial translation of the connector 526 in response to rotation of the driver 530. The end cap guide 536 may include an elongate member extending proximally from an end cap 534 configured to couple to the distal end 512B of housing 512. FIG. 16 depicts an exploded perspective view of the end cap 534 having the end cap guide 536 extending proximally therefrom. The end cap 534 may include an external threading configured to threadably engage internal threads at the distal end 512B of the housing 512. The end cap 534 and the end cap guide 536 may be rotationally fixed relative to the housing 512. The end cap guide 536 may be configured to inhibit rotation of the distal portion 526B of the connector 526 to guide axial translation of the connector 526 in response to rotation of driver 530.

Figure 18:
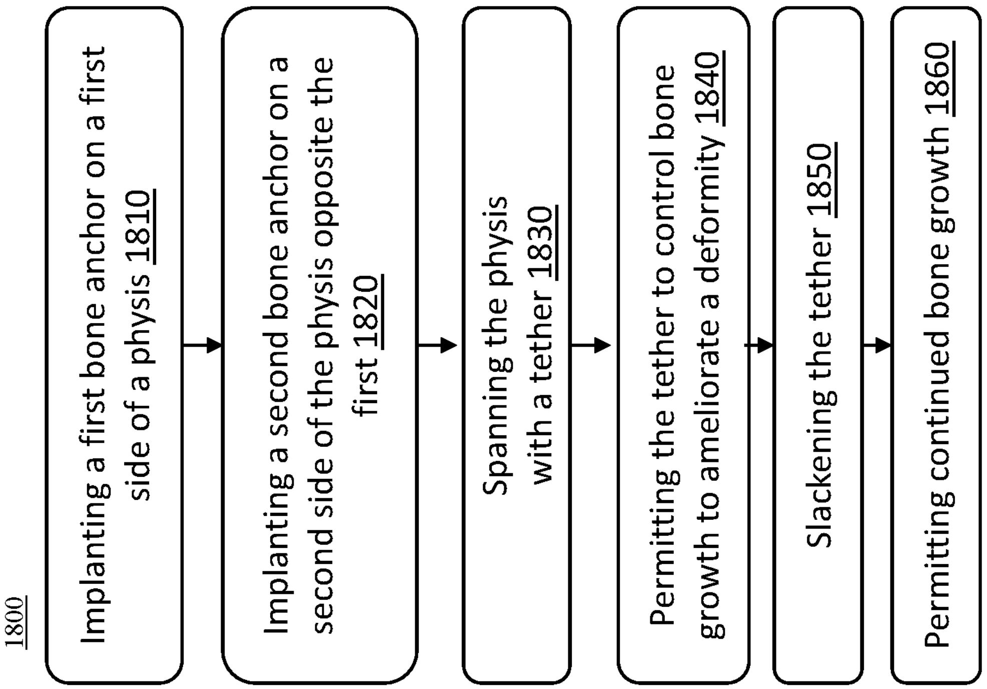
FIG. 18 illustrates a method for correcting a deformity.

FIG. 18 illustrates an example method 1800 for correcting a deformity. The method can begin with operation 1810.

Operation 1810 includes implanting a first bone anchor on a first side of a physis of a patient. The physis can be a growth plate of the patient, such as a growth plate proximate a skeletal deformity of a patient. This can include forming one or more incisions in the patient. The first bone anchor can be implanted through the one or more incisions. The first bone anchor can be, for example, a static bone anchor (e.g., bone anchor 104) or an adjustable bone anchor (e.g., bone anchor 106, 206, 306). Following operation 1810, the flow of the method can move to operation 1820.

Operation 1820 includes implanting a second bone anchor on a second side of the physis opposite the first 1820. This can include forming one or more incisions in the patient (e.g., the incisions can be the same as or different from the incisions in operation 1810). The second bone anchor can be implanted through the one or more incisions. The second bone anchor can be, for example, a static bone anchor (e.g., bone anchor 104) or an adjustable bone anchor (e.g., bone anchor 106, 206, 306). Following operation 1820, the flow of the method can move to operation 1830.

Operation 1830 includes spanning the physis with a tether. The tether can be, for example, the tether 102. In some examples, this includes coupling the tether to one or both of the bone anchors. In some examples, the tether is integral with or preinstalled into one of the bone anchors and the operation 1830 includes coupling the tether to the other bone anchor. In some examples the coupling can be such that an amount of tension is added to the tether. In some examples, after the tether is attached to both bone anchors, a tension in the tether is adjusted (e.g., increased or decreased). Following operation 1830, the flow of the method can move to operation 1840.

Figure 19:
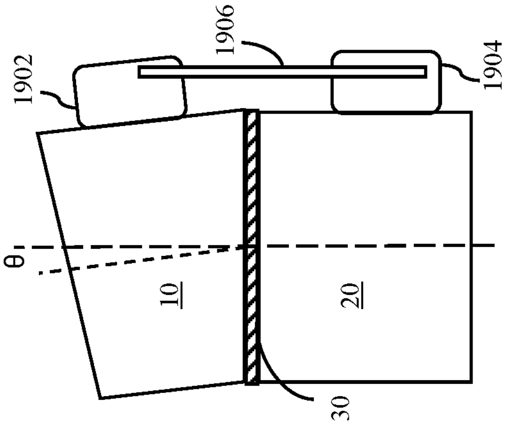
FIG. 19 illustrates an example arrangement of bone sections, physis, bone anchors, and tether at a first time.

FIG. 19 illustrates an example arrangement following operation 1830. As illustrated, there is a first bone anchor 1902 implanted in a first bone section 10, a second bone anchor 1904 implanted in a second bone section 20, and a tether 1906 spanning the physis 30 between the bone sections 10, 20. As can be seen, there is an angular deformity in the bone 10 of 0 degrees. As further illustrated, there are measurements x and y that can be used to identify changes in anatomy over time.

Returning to FIG. 18, operation 1840 includes permitting the tether to control bone growth to ameliorate a deformity. This operation 1840 can occur, for example, after closing any incisions formed in the prior operations. The patient's bone will grow proximate to the physis, but the tension of the tether controls the growth of new bone in such a way that the patient's deformity is lessened. Following operation 1840, the flow of the method can move to operation 1850.

Figure 20:
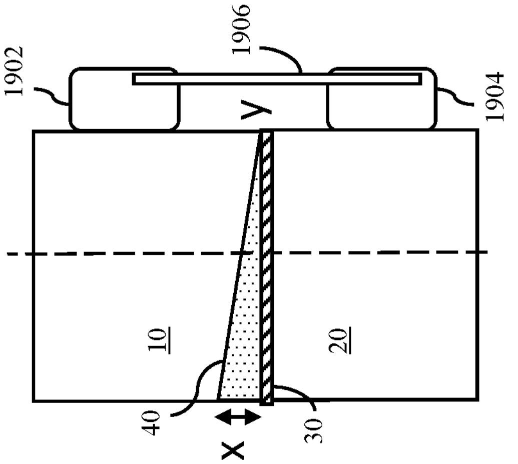
FIG. 20 illustrates an example arrangement of FIG. 19 at a second time.

FIG. 20 illustrates an example arrangement following operation 1840. New bone growth region 40 is now present compared to FIG. 19. The constraints of the tethering system has resulted in asymmetric bone growth from the physis 30. In the region furthest from the tethering system, new bone growth measures x units and in the region closest to the tethering system, new bone growth is y units, where x>y. In the illustrated example, measurement y is substantially zero. The asymmetric growth has reduced the deformity angle from 0 degrees about 0 degrees, though in practice some deformity may still exist but be lessened.

Returning to FIG. 18, operation 1850 includes slackening the tether. This operation can be performed postoperatively (e.g., after any incisions from operations 1810 and 1820 have closed or healed). The slackening can be performed by non-invasively actuating an adjustable bone anchor implanted in one or both of steps 1810 and 1820. The actuating can be performed transcutaneously. For instance, the actuating can be performed by rotating one or more internal magnets of the first or second bone anchor by rotating one or more external magnets of an external adjustment device. Actuating the actuator can cause a clamp to release the tether, thereby slackening the tether. In addition or instead, actuating the actuator can cause a spool to unspool the tether, thereby slackening the tether. In addition or instead, actuating the actuator can unlock a structure to permit the tether to slacken (e.g., as a result of natural growth proximate the physis). In addition to or instead of actuation with magnets, an external remote control can cause an internal motor to actuate, such as by sending a signal interpretable by internal circuitry of an actuatable bone anchor as an indication to actuate. Following operation 1850, the flow of the method can move to operation 1860.

Operation 1860 includes permitting continued bone growth. Continued bone growth of the patient proximate the physis. In contrast to the bone growth in operation 1830, now the tether is slackened or unconstrained and bone growth can continue without being substantially controlled (e.g., controlled less than it was when the tether was in the state it was in during operation 1830) by the tether.

Figure 21:
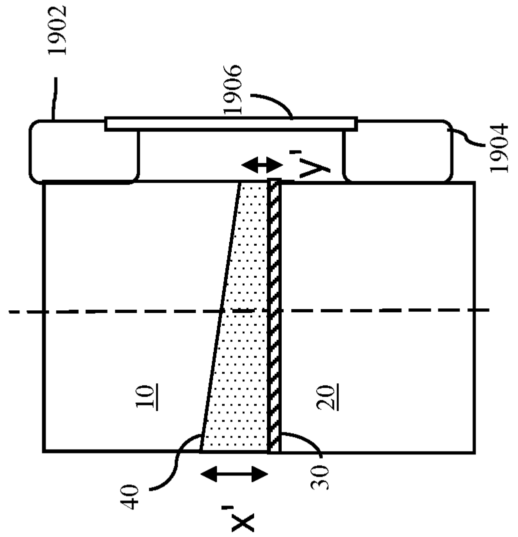
FIG. 21 illustrates an example arrangement of FIG. 19 at a third time.

FIG. 21 illustrates an example arrangement following operation 1860. Following bone growth in operation 1860, the size of distance x has become x' and y has become y'. Due to constrains by the anchors 1902, 1904 and tether 1906 being lessened in operation 1850, y'>y and x'>x.

Figure 22:
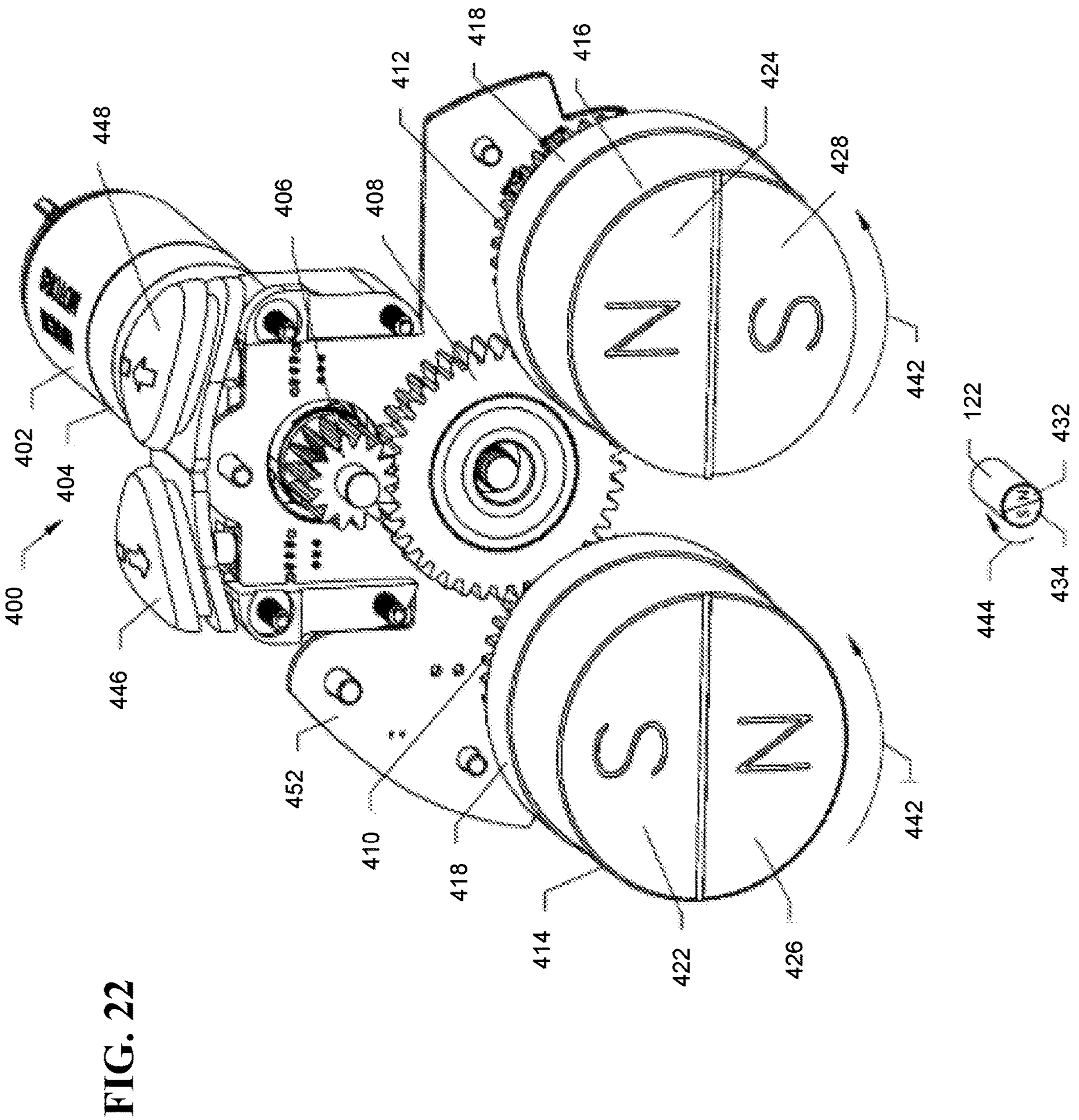
FIG. 22 shows the internal components of an external adjustment device for non-invasively adjusting a distraction and compression device according to embodiments of the invention.
Figure 23:
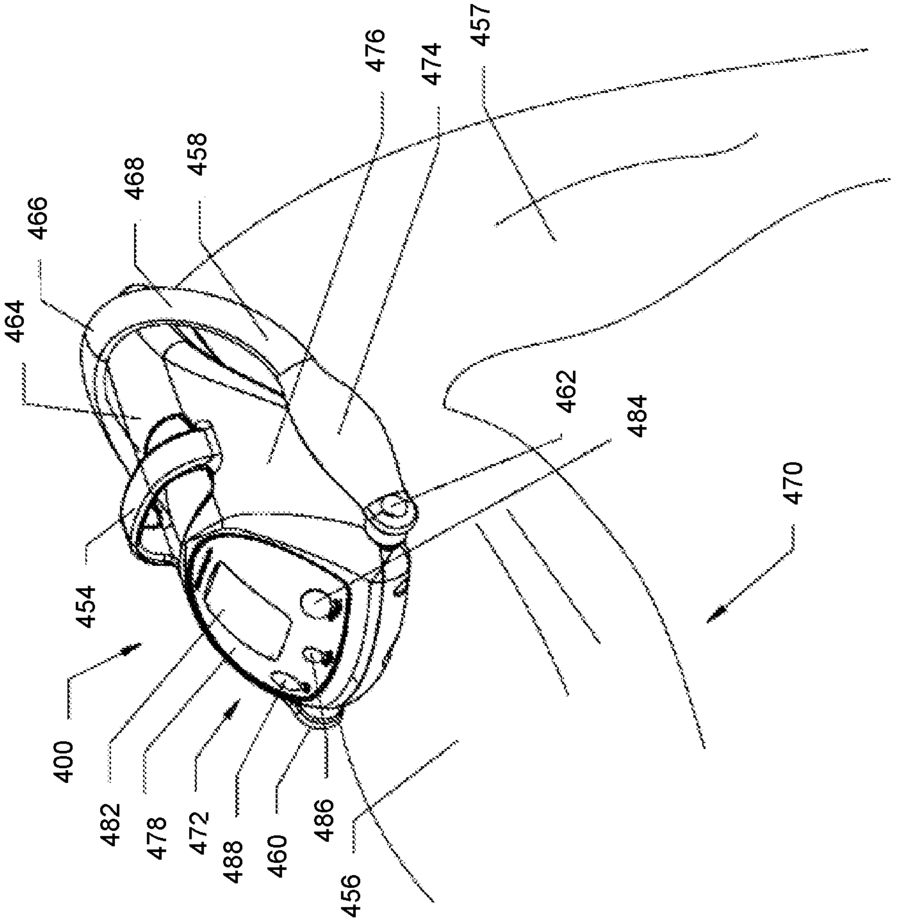
FIGS. 23 and 24 show external adjustment devices in configurations for adjusting a distraction and compression device implanted within a femur, and within a tibia, respectively, in accordance with embodiments of the invention.
Figure 24:
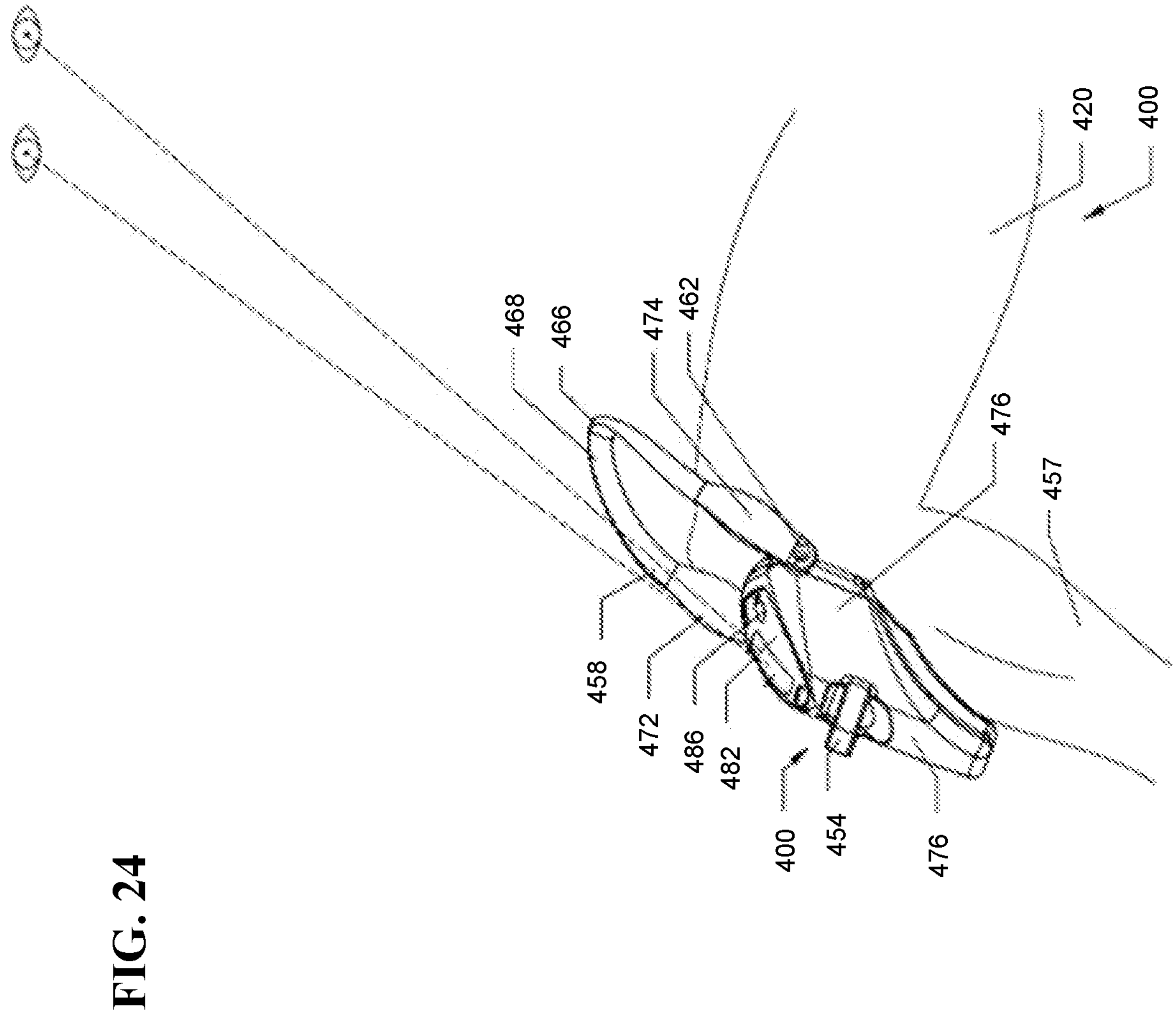

FIGS. 22-24 illustrate an external adjustment device 400 configured for applying a moving magnetic field to allow for non-invasive adjustment of the implant system 100 by turning a driver 122 within the implant system 100, as described. External adjustment device 400 may also be referred to as an external remote controller or external remote control device, and may operate analogously with respect to drivers 218, 318, 530 within implant systems 200, 300, 500 respectively. FIG. 22 illustrates the internal components of the external adjustment device 400, and for clear reference, shows the driver 122 of the implant system 100 (as representative of drivers and implant systems disclosed herein) without the rest of the assembly. The internal working components of the external adjustment device 400 may, in certain embodiments, be similar to those described in U.S. Patent Application Publication No. 2012/0004494, which is incorporated by reference herein. A motor 402 with a gear box 404 outputs to a motor gear 406. The motor gear 406 engages and turns central (idler) gear 408, which has the appropriate number of teeth to turn first and second magnet gears 410, 412 at identical rotational speeds. First and second magnets 414, 416 turn in unison with the first and second magnet gears 410, 412, respectively. Each magnet 414, 416 is held within a respective magnet cup 418 (shown partially). An exemplary rotational speed may be 60 RPM or less. This speed range may be configured to limit the amount of current density induced in the body tissue and fluids, to meet international guidelines or standards. As seen in FIG. 22, the south pole 422 of the first magnet 414 is oriented the same as the north pole 424 of the second magnet 416, and likewise, the first magnet 414 has its north pole 426 oriented the same as the south pole 428 of the second magnet 416. As these two magnets 414, 416 turn synchronously together, they apply a complementary and additive moving magnetic field to the radially-poled, driver 122, having a north pole 432 and a south pole 434. Magnets having multiple north poles (for example, two) and multiple south poles (for example, two) are also contemplated in each of the devices. As the two magnets 414, 416 turn in a first rotational direction 442 (e.g., counter-clockwise), the magnetic coupling causes the driver 122 to turn in a second, opposite rotational direction 444 (e.g., clockwise). The rotational direction of the motor 402 and corresponding rotational direction of the magnets 414, 416 is controlled by buttons 446, 448. One or more circuit boards 452 contain control circuitry for both sensing rotation of the magnets 414, 416 and controlling the rotation of the magnets 414, 416.

FIGS. 23 and 24 show the external adjustment device 400 for use with a device placed in the femur (FIG. 23) or the tibia (FIG. 24). The external adjustment device 400 has a first handle 454 for carrying or for steadying the external adjustment device 400, for example, steadying it against an upper leg 456 (as in FIG. 23) or lower leg 457 as in (FIG. 24). An adjustable handle 458 is rotationally attached to the external adjustment device 400 at pivot points 460, 462. Pivot points 460, 462 have easily lockable/unlockable mechanisms, such as a spring-loaded brake, ratchet or tightening screw, so that a desired angulation of the adjustable handle 458 in relation to housing 464 can be adjusted and locked in orientation. Adjustable handle 458 is shown in two different positions in FIGS. 23 and 24. In FIG. 23, adjustable handle 458 is set so that apex 466 of loop 468 rests against housing 464. In this position, patient 470 is able to hold onto one or both of grips 472, 474 while the adjustment procedure (for example transporting bone between 0.10 mm to 1.50 mm) is taking place. It is contemplated that the procedure could also be a lengthening procedure for a bone lengthening device or a lengthening procedure for a lengthening plate which is attached external to the bone. Turning to FIG. 24, when the bone transport implant system 100 is implanted in a tibia, the adjustable handle 458 may be changed to a position in which the patient 470 can grip onto the apex 466 so that the magnet area 476 of the external adjustment device 400 is held over the portion of the implant system 100 containing the driver 122. In both cases, the patient 470 is able to clearly view control panel 478 including a display 482. In a different configuration from the two directional buttons 446, 448 in FIG. 22, the control panel 478 includes a start button 484, a stop button 486 and a mode button 488. Control circuitry contained on circuit boards 452 may be used by the surgeon to store important information related to the specific aspects of each particular patient. For example, in some patients an implant may be placed antegrade into the tibia. In other patients the implant may be placed either antegrade or retrograde about the femur. In each of these three cases, it may be desired to move the bone either from distal to proximal or from proximal to distal. By having the ability to store information of this sort that is specific to each particular patient within the external adjustment device 400, the external adjustment device 400 can be configured to direct the magnets 414, 416 to turn in the correct direction automatically, while the patient need only place the external adjustment device 400 at the desired position, and push the start button 484. The information of the maximum allowable bone transport length per day and maximum allowable bone transport length per session can also be input and stored by the surgeon for safety purposes. These may also be added via an SD card or USB device, or by wireless input. An additional feature is a camera at the portion of the external adjustment device 400 that is placed over the skin. For example, the camera may be located between first magnet 414 and second magnet 416. The skin directly over the implanted driver 122 may be marked with indelible ink. A live image from the camera is then displayed on the display 482 of the control panel 478, allowing the user to place the first and second magnets 414, 416 directly over the area marked on the skin. Crosshairs can be overlaid on the display 482 over the live image, allowing the user to align the mark on the skin between the crosshairs, and thus optimally place the external adjustment device 400.

Other external adjustment devices can be used to cause actuation of the distraction devices described herein. Such external adjustment devices include, for example, those described in U.S. Pat. No. 8,382,756 filed on Nov. 20, 2009, U.S. Pat. No. 9,248,043 filed Jun. 29, 2011, U.S. Pat. No. 9,078,711 filed on Jun. 6, 2012, U.S. Pat. No. 9,044,281 filed on Oct. 18, 2012, U.S. application Ser. No. 14/698,665 filed on Apr. 28, 2015, U.S. application Ser. No. 14/932,904 filed on Nov. 4, 2015, U.S. Ser. No. 16/004,099 filed on Dec. 12, 2016, and App. No. PCT/US2020/017338 filed on Feb. 7, 2020, all of which are incorporated herein by reference as if set forth in their entirety.

While implementations above are primarily in the context of externally magnetically driven systems, other drive systems can be used. For example, in addition to or instead of the magnet-based driving, one or more of the drive elements can take the form of an implanted electric motor. The implanted electric motor can be powered by an external power source (e.g., via a radiofrequency link, via an ultrasonic energy transfer technique, via an inductive connection, via another technique, or via combinations thereof) or an implanted power source (e.g., a battery or charging capacitor, which may be charged by the external power source). The implanted power source may be within the implant (e.g., within a housing thereof) or separate from the implant and coupled to the implant via a cable.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups. As used herein, "substantially" refers to largely, for the most part, entirely specified or any slight deviation which provides the same technical benefits of the disclosure.

Embodiments of the present disclosure may include the following features:

1. An implant system, comprising: a tether having a first end opposite a second end; a fixed bone anchor configured to couple to the first end of the tether; and an adjustable bone anchor configured to couple to the second end of the tether, the adjustable bone anchor including: a housing extending between a distal end and a proximal end of the adjustable bone anchor, a driver disposed within the housing, wherein the driver is configured to drive rotational motion, an output shaft extending proximally from the driver, a screw cap disposed at the proximal end of the adjustable bone anchor, and a clamping mechanism having a lower portion configured to rotatably engage the output shaft, and an upper portion configured to couple to an inner surface of the screw cap, wherein the lower portion is configured to translate within the housing in response to rotation by the driver relative to the lower portion, wherein the clamping mechanism is configured to secure the adjustable bone anchor to the tether.

Item 2. The implant system of item 1, wherein the driver comprises a rotatable permanent magnet configured to be rotated by an externally applied magnetic field.

Item 3. The implant system of item 2, further comprising an external adjustment device including an external magnet configured to actuate the rotatable permanent magnet.

Item 4. The implant system of item 3, wherein the external magnet is configured to rotate in a first direction corresponding to locking the clamping mechanism and to rotate in a second direction corresponding to unlocking the clamping mechanism.

Item 5. The implant system of item 1, wherein the fixed bone anchor comprises a plate coupled to a proximal end of an externally threaded screw, the plate including an attachment feature configured to couple to the first end of the tether.

Item 6. The implant system of item 1, wherein the adjustable bone anchor includes an externally threaded portion configured to engage bone.

Item 7. The implant system of item 1, wherein at least a portion of the tether extends through the adjustable bone anchor between the upper portion and the lower portion of the clamping mechanism.

Item 8. The implant system of item 1, wherein the clamping mechanism is configured to engage or disengage the tether to increase or decrease tension on the tether, respectively.

Item 9. The implant system of item 8, wherein the clamping mechanism is configured to engage or disengage the tether in response to actuation of the driver.

Item 10. The implant system of item 9, wherein the output shaft is configured to cause the lower portion of the clamping mechanism to translate proximally to engage and distally to disengage the upper portion of the clamping mechanism in response to actuation of the driver.

Item 11. The implant system of item 1, wherein the upper and lower portions of the clamping mechanism each include a flat surface.

Item 12. The implant system of item 1, wherein one of the upper portion and the lower portion of the clamping mechanism includes a feature having a triangular cross sectional shape, and the other of the upper portion and the lower portion includes a recess configured to receive the triangular cross sectional shaped feature.

Item 13. The implant system of item 1, wherein one of the upper portion and the lower portion of the clamping mechanism includes a barbed surface, and the other of the upper portion and the lower portion includes a recess configured to receive the barbed surface.

Item 14. The implant system of item 1, wherein one of the upper portion and the lower portion of the clamping mechanism comprises two features, each having a triangular cross sectional shape, and the other one of the upper portion and the lower portion comprises two recesses configured to receive the features having the triangular cross sectional shape.

Item 15. The implant system of item 1, wherein the screw cap comprises at least one aperture configured to laterally receive the tether therethrough.

Item 16. The implant system of item 15, wherein the at least one aperture further comprises a pair of apertures, and wherein the clamping mechanism is positioned laterally between the pair of apertures, such that the tether extends through the pair of apertures and between the upper portion and the lower portion of the clamping mechanism.

Item 17. The implant system of item 1, wherein the adjustable bone anchor includes a bone engagement surface adjacent the distal end configured to engage a bone.

Item 18. The implant system of item 1, wherein the lower portion of the clamping mechanism includes an internally threaded portion configured to engage an externally threaded portion of the output shaft.

Item 19. The implant system of item 1, wherein the fixed bone anchor and the adjustable bone anchor comprise a biocompatible material.

Item 20. The implant system of item 1, wherein the tether comprises a biocompatible material.

Item 21. The implant system of item 1, wherein the fixed bone anchor and the adjustable bone anchor comprise titanium, and wherein the tether comprises polyethylene.

Item 22. An implant system, comprising: a tether having a first end and a second end; a fixed bone anchor configured to couple to bone and the first end of the tether; and an adjustable bone anchor configured to couple to bone and the second end of the tether, the adjustable bone anchor including: a housing extending between a distal end and a proximal end of the adjustable bone anchor, a driver disposed within the housing, wherein the driver is configured to drive rotational motion, an output shaft extending proximally from the driver, a locking mechanism disposed within the housing, the locking mechanism including a distal portion with proximal facing teeth, and a proximal portion comprising a spool and a plurality of teeth extending distally therefrom, wherein the distal portion is configured to rotatably engage with the output shaft, and to translate in response to rotation of the output shaft, a spool extending proximally from the proximal portion of the locking mechanism, wherein the second end of the tether is configured to wrap around the spool.

Item 23. The implant system of item 22, wherein the driver comprises a rotatable permanent magnet configured to be rotated by an externally applied magnetic field.

Item 24. The implant system of item 23, further comprising an external adjustment device including an external magnet configured to actuate the rotatable permanent magnet of the adjustable bone anchor and displace the distal portion of the locking mechanism to engage or disengage the proximal portion of the locking mechanism.

Item 25. The implant system of item 24, wherein the external magnet is configured to rotate in a first direction corresponding to a locked position of the locking mechanism and rotate in a second direction corresponding to an unlocked position of the locking mechanism.

Item 26. The implant system of item 25, wherein the spool freely rotates in the unlocked position about an axis that is substantially aligned with an axis of rotation of the rotatable permanent magnet.

Item 27. The implant system of item 22, wherein the adjustable bone anchor includes an externally threaded portion configured to engage cortical bone.

Item 28. The implant system of item 22, wherein the adjustable bone anchor includes a bone engagement surface adjacent the distal end configured to engage a bone.

Item 29. The implant system of item 22, wherein the distal portion of the locking mechanism includes an internally threaded portion configured to engage an externally threaded portion of the output shaft.

Item 30. The implant system of item 22, wherein the fixed bone anchor comprises a plate configured to threadably engage an externally threaded screw, the plate including an attachment feature configured to couple to the first end of the tether.

Item 31. The implant system of item 23, wherein the adjustable bone anchor comprises a second rotatable permanent magnet configured to rotate the spool.

Item 32. The implant system of item 31, wherein the second rotatable permanent magnet is configured to rotate in a first direction to wind the tether around the spool and rotate in a second direction to unwind the tether from the spool.

Item 33. The implant system of item 31, wherein the second rotatable permanent magnet is disposed within a cavity in the spool.

Item 34. The implant system of item 22, wherein the adjustable bone anchor comprises a screw cap coupled to the proximal end, the screw cap having a guide slot configured to receive a portion of the tether therethrough.

Item 35. The implant system of item 34, wherein a proximal portion of the spool is disposed within a recess of the screw cap.

Item 36. The implant system of item 22, wherein the fixed bone anchor and the adjustable bone anchor comprise a biocompatible material.

Item 37. The implant system of item 22, wherein the tether comprises a biocompatible material.

Item 38. The implant system of item 22, wherein the fixed bone anchor and the adjustable bone anchor comprise titanium, and wherein the tether comprises polyethylene.

Item 39. An implant system, comprising: a tether having a first end and a second end; a fixed bone anchor configured to couple to the first end of the tether; and an adjustable bone anchor configured to couple to the second end of the tether, the adjustable bone anchor including: a housing extending between a distal end and a proximal end of the adjustable bone anchor, a driver disposed within the housing, wherein the driver is configured to drive rotational motion, a gear system coupled to a proximal end of the driver, and an output member coupled to the gear system, the output member including a spool configured to receive the tether.

Item 40. The implant system of item 39, wherein the driver comprises a rotatable permanent magnet configured to be rotated by an externally applied magnetic field.

Item 41. The implant system of item 40, further comprising an external adjustment device including an external magnet configured to actuate the rotatable permanent magnet of the adjustable bone anchor to rotate the spool.

Item 42. The implant system of item 41, wherein the external magnet is configured to rotate in a first direction wind the tether around the spool and rotate in a second direction to unwind the tether from the spool.

Item 43. The implant system of item 40, wherein the rotatable permanent magnet includes a D-shaped cross sectional shape.

Item 44. The implant system of item 40, wherein the adjustable bone anchor includes a magnet brake coupled to a distal end of the rotatable permanent magnet.

Item 45. The implant system of item 39, wherein the adjustable bone anchor includes an end cap configured to seal the housing at a proximal end thereof, and the adjustable bone anchor includes a guide slot disposed proximally relative to the end cap, wherein the guide slot is in communication with the spool and is configured to laterally receive the tether therethrough.

Item 46. The implant system of item 45, wherein the guide slot is configured to engage a driver tool to implant the adjustable bone anchor in a bone.

Item 47. The implant system of item 45, wherein a second end of the tether couples to the output member, and a portion of the tether is configured to wrap around the spool.

Item 48. The implant system of item 45, further comprising epoxy to seal the end cap to the housing.

Item 49. The implant system of item 39, wherein the adjustable bone anchor includes an externally threaded portion configured to engage cortical bone.

Item 50. The implant system of item 39, wherein the adjustable bone anchor includes a bone engagement surface adjacent the distal end configured to engage a bone.

Item 51. The implant system of item 39, wherein the fixed bone anchor comprises an externally threaded screw, and a plate having an internally threaded aperture configured to engage the externally threaded screw and an attachment feature configured to couple to the first end of the tether.

Item 52. The implant system of item 39, wherein the fixed bone anchor and the adjustable bone anchor comprise a biocompatible material.

Item 53. The implant system of item 39, wherein the tether comprises a biocompatible material.

Item 54. The implant system of item 39, wherein the fixed bone anchor and the adjustable bone anchor comprise titanium, and wherein the tether comprises polyethylene.

Item 55. The implant system of item 39, wherein the gear system comprises one or more stages of planetary gears.

Item 56. The implant system of item 55, wherein the gear system comprises two or more stages of planetary gears.

Item 57. The implant system of item 56, wherein the gear system comprises three or more stages of planetary gears.

Item 58. The implant system of item 57, wherein the gear system comprises four stages of planetary gears.

Item 59. The implant system of item 55, wherein each stage of the one or more stages of planetary gears provides a 4:1 torque multiplier.

Item 60. The implant system of item 39, wherein the adjustable bone anchor is configured to release existing tension on the tether.

Item 61. An implant system, comprising: a fixed bone anchor; a tether having a first end coupled to the fixed bone anchor; and an adjustable bone anchor coupled to a second end of the tether, the adjustable bone anchor including: a housing extending between a distal end and a proximal end of the adjustable bone anchor; a driver disposed within the housing; an output member configured to be rotated by the driver, the output member including an internally threaded portion; a connector comprising a distal portion disposed within and in threaded engagement with the output member, and a proximal portion coupled to the second end of the tether, wherein the connector is configured to translate relative to the output member to adjust the tether; and a first plate coupled to the proximal end of the adjustable bone anchor, the plate including a first aperture configured to receive the proximal portion of the connector, and a first attachment feature configured to couple to the tether at a first point between the first end and the second end thereof.

Item 62. The implant system of item 61, wherein the driver comprises a rotatable permanent magnet configured to be rotated by an externally applied magnetic field.

Item 63. The implant system of item 62, wherein the rotatable permanent magnet includes a D-shaped cross sectional shape.

Item 64. The implant system of item 62, further comprising an external adjustment device including an external magnet configured to actuate the rotatable permanent magnet of the adjustable bone anchor to distally or proximally displace the connector to increase or decrease tension in the tether, respectively.

Item 65. The implant system of item 64, wherein the external magnet is configured to rotate in a first direction corresponding to distal translation of the connector and rotate in a second direction corresponding to proximal translation of the connector.

Item 66. The implant system of item 61, wherein the fixed bone anchor includes a second plate configured to threadably engage a screw, the second plate comprising a second aperture configured to couple to the first end of tether and a second attachment feature configured to couple to the tether at a second point between the first end and the second end thereof.

Item 67. The implant system of item 61, wherein the connector is configured to translate distally or proximally to increase or decrease tension of the tether, respectively.

Item 68. The implant system of item 61, wherein the proximal portion of the connector is spherical or substantially spherical.

Item 69. The implant system of item 61, wherein the adjustable bone anchor includes an externally threaded portion configured to engage cortical bone.

Item 70. The implant system of item 61, wherein the adjustable bone anchor includes a bone engagement surface adjacent the distal end configured to engage a bone.

Item 71. The implant system of item 61, wherein the fixed bone anchor and the adjustable bone anchor comprise a biocompatible material.

Item 72. The implant system of item 61, wherein the tether comprises a biocompatible material.

Item 73. The implant system of item 61, wherein the fixed bone anchor and the adjustable bone anchor comprise titanium, and wherein the tether comprises polyethylene.

Item 74. An implant system comprising: a tether; a first bone anchor; a second bone anchor, wherein the second bone anchor is configured to be transcutaneously actuated post-operatively through intact skin to slacken the tether, when the tether connects the first bone anchor and the second bone anchor.

Item 75. The implant system of item 74, wherein the second bone anchor comprises a clamp configured to grasp the tether; and wherein the clamp is configured to release the grasp on the tether in response to sufficient transcutaneous actuation.

Item 76. The implant system of item 74, wherein the second bone anchor comprises a spool configured to hold a wound section of the tether; and wherein the spool is configured to unwind in response to sufficient transcutaneous actuation.

Item 77. A method comprising: slackening a growth-plate-spanning tether coupled to a first anchor by post-operatively and non-invasively actuating an actuator of the first anchor implanted in a patient.

Item 78. The method of item 77, further comprising: implanting the first anchor in the patient on a first side of a growth plate; implanting a second anchor in the patient on a second side of the growth plate opposite the first side; and coupling the first anchor and the second anchor with the tether, such that the tether spans the growth plate.

Item 79. The method of item 78, further comprising: forming one or more incisions in the patient, wherein the implanting of the first anchor and the second anchor occur through the one or more incisions; and closing the one or more incisions, wherein the slackening occurs after closing the one or more incisions.

Item 80. The method of item 78, wherein the first anchor, the second anchor, and the tether cooperate to control new bone growth of the growth plate to correct a deformity of the patient.

Item 81. The method of item 77, wherein actuating the actuator cause a clamp to release the tether, thereby slackening the tether.

Item 82. The method of item 77, wherein actuating the actuator cause a spool to unspool the tether, thereby slackening the tether.

Item 83. The method of item 77, wherein the actuating of the actuator occurs through transcutaneously through intact skin.

Item 84. The method of item 77, further comprising: rotating one or more internal magnets of the first anchor by rotating one or more external magnets of an external adjustment device, thereby post-operatively and non-invasively actuating the actuator.

Item 85. The method of item 77, wherein the growth plate is active.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and subcombinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. An implant system, comprising:

a tether having a first end opposite a second end;

a fixed bone anchor configured to couple to the first end of the tether; and an adjustable bone anchor configured to couple to the second end of the tether, the adjustable bone anchor including:

a housing extending between a distal end and a proximal end of the adjustable bone anchor, a driver disposed within the housing, wherein the driver is configured to drive rotational motion, an output shaft extending proximally from the driver, a screw cap disposed at the proximal end of the adjustable bone anchor, and a clamping mechanism having a lower portion configured to rotatably engage the output shaft, and an upper portion configured to couple to an inner surface of the screw cap, wherein the lower portion is configured to translate within the housing in response to rotation by the driver relative to the lower portion, wherein the clamping mechanism is configured to secure the adjustable bone anchor to the tether.

2. The implant system of claim 1, wherein the driver comprises a rotatable permanent magnet configured to be rotated by an externally applied magnetic field.

3. The implant system of claim 2, further comprising an external adjustment device including an external magnet configured to actuate the rotatable permanent magnet.

4. The implant system of claim 3, wherein the external magnet is configured to rotate in a first direction corresponding to locking the clamping mechanism and to rotate in a second direction corresponding to unlocking the clamping mechanism.

5. The implant system of claim 1, wherein the fixed bone anchor comprises a plate coupled to a proximal end of an externally threaded screw, the plate including an attachment feature configured to couple to the first end of the tether.

6. The implant system of claim 1, wherein the adjustable bone anchor includes an externally threaded portion configured to engage bone.

7. The implant system of claim 1, wherein at least a portion of the tether extends through the adjustable bone anchor between the upper portion and the lower portion of the clamping mechanism.

8. The implant system of claim 1, wherein the clamping mechanism is configured to engage or disengage the tether to increase or decrease tension on the tether, respectively.

9. The implant system of claim 8, wherein the clamping mechanism is configured to engage or disengage the tether in response to actuation of the driver.

10. The implant system of claim 9, wherein the output shaft is configured to cause the lower portion of the clamping mechanism to translate proximally to engage and distally to disengage the upper portion of the clamping mechanism in response to actuation of the driver.

11. The implant system of claim 1, wherein the upper and lower portions of the clamping mechanism each include a flat surface.

12. The implant system of claim 1, wherein one of the upper portion and the lower portion of the clamping mechanism includes a feature having a triangular cross sectional shape, and the other of the upper portion and the lower portion includes a recess configured to receive the triangular cross sectional shaped feature.

13. The implant system of claim 1, wherein one of the upper portion and the lower portion of the clamping mechanism includes a barbed surface, and the other of the upper portion and the lower portion includes a recess configured to receive the barbed surface.

14. The implant system of claim 1, wherein one of the upper portion and the lower portion of the clamping mechanism comprises two features, each having a triangular cross sectional shape, and the other one of the upper portion and the lower portion comprises two recesses configured to receive the features having the triangular cross sectional shape.

15. The implant system of claim 1, wherein the screw cap comprises at least one aperture configured to laterally receive the tether therethrough.

16. The implant system of claim 15, wherein the at least one aperture further comprises a pair of apertures, and wherein the clamping mechanism is positioned laterally between the pair of apertures, such that the tether extends through the pair of apertures and between the upper portion and the lower portion of the clamping mechanism.

17. The implant system of claim 1, wherein the adjustable bone anchor includes a bone engagement surface adjacent the distal end configured to engage a bone.

18. The implant system of claim 1, wherein the lower portion of the clamping mechanism includes an internally threaded portion configured to engage an externally threaded portion of the output shaft.

19. The implant system of claim 1, wherein the fixed bone anchor, the adjustable bone anchor, and the tether comprise a biocompatible material.

20. The implant system of claim 1, wherein the fixed bone anchor and the adjustable bone anchor comprise titanium, and wherein the tether comprises polyethylene.

* * * * *